United States Patent
Burnet et al.

(10) Patent No.: US 8,143,294 B2
(45) Date of Patent: Mar. 27, 2012

(54) 2-SULFANYL-SUBSTITUTED IMIDAZOLE DERIVATIVES AND THEIR USE AS CYTOKINE INHIBITORS

(76) Inventors: Michael Burnet, Tuebingen (DE); Stefan Laufer, Tuebingen (DE); Pierre Koch, Altensteig (DE)

( * ) Notice: Subject to any disclaimer, the term of this patent is extended or adjusted under 35 U.S.C. 154(b) by 441 days.

(21) Appl. No.: 12/347,498

(22) Filed: Dec. 31, 2008

(65) Prior Publication Data

US 2009/0270462 A1 Oct. 29, 2009

Related U.S. Application Data

(60) Provisional application No. 61/009,556, filed on Dec. 31, 2007.

(51) Int. Cl.
*C07D 401/04* (2006.01)
*A61K 31/4439* (2006.01)

(52) U.S. Cl. .................... 514/341; 546/274.4
(58) Field of Classification Search .................. None
See application file for complete search history.

(56) References Cited

U.S. PATENT DOCUMENTS

| | | | |
|---|---|---|---|
| 6,432,988 B1 | 8/2002 | Laufer et al. |
| 7,253,191 B2 | 8/2007 | Laufer et al. |
| 7,442,713 B2 | 10/2008 | Laufer et al. |
| 7,582,660 B2 | 9/2009 | Laufer et al. |

FOREIGN PATENT DOCUMENTS

| | | |
|---|---|---|
| WO | WO00/17192 | 3/2000 |
| WO | WO02/066458 | 8/2002 |
| WO | WO03/097633 | 11/2003 |
| WO | WO2004/018458 | 3/2004 |
| WO | WO2006/089798 | 8/2006 |
| WO | WO2008/023066 | 2/2008 |

*Primary Examiner* — Zinna Northington Davis
(74) *Attorney, Agent, or Firm* — Edwards Wildman Palmer LLP; Jeffrey D. Hsi; Mark D. Russett

(57) ABSTRACT

The invention relates to 2-thio-substituted imidazole derivatives of the Formula I, and to methods of use thereof.

11 Claims, No Drawings

2-SULFANYL-SUBSTITUTED IMIDAZOLE DERIVATIVES AND THEIR USE AS CYTOKINE INHIBITORS

CROSS-REFERENCE TO RELATED APPLICATIONS

This application claims the benefit of priority to U.S. Provisional Patent Application No. 61/009,556, filed Dec. 31, 2007, the contents of which are incorporated herein in their entirety.

FIELD OF THE INVENTION

This invention relates to substituted imidazoles, compositions thereof, and methods for treating conditions including inflammatory disorders.

BACKGROUND OF THE INVENTION

Mitogen-activated protein (MAP) kinases is a family of proline-directed serine/threonine kinases that activate their substrates by dual phosphorylation. The kinases are activated by a variety of signals including nutritional and osmotic stress, UV light, growth factors, endotoxin and inflammatory cytokines. The p38 MAP kinase group is a MAP family of various isoforms, including p38α, p38β and p38γ, and is responsible for phosphorylating and activating transcription factors (e.g. ATF2, CHOP and MEF2C) as well as other kinases (e.g. MAPKAP-2 and MAPKAP-3). The p38 isoforms are activated by bacterial lipopolysaccharide (endotoxin), physical and chemical stress and by pro-inflammatory cytokines, including tumor necrosis factor (TNF-a) and interleukin-1 (IL-1). The products of the p38 phosphorylation mediate the production of inflammatory cytokines, including TNF and IL-1, and cyclooxygenase-2.

TNF-α is a cytokine produced primarily by activated monocytes and macrophages. Excessive or unregulated TNF production has been implicated in mediating a number of diseases. Recent studies indicate that TNF has a causative role in the pathogenesis of rheumatoid arthritis. Additional studies demonstrate that inhibition of TNF has broad application in the treatment of inflammation, inflammatory bowel disease, multiple sclerosis and asthma.

TNF has also been implicated in viral infections, such as HIV, influenza virus, and herpes virus including herpes simplex virustype-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitis, among others.

IL-8 is another pro-inflammatory cytokine, which is produced by mononuclear cells, fibroblasts, endothelial cells, and keratinocytes, and is associated with conditions associated with inflammation.

IL-1 is produced by activated monocytes and macrophages and is involved in the inflammatory response. IL-1 plays a role in many pathophysiological responses including rheumatoid arthritis, fever and reduction of bone resorption.

TNF, IL-1 and IL-8 affect a wide variety of cells and tissues and are important inflammatory mediators of a wide variety of disease states and conditions. The inhibition of these cytokines by inhibition of the p38 kinase is of benefit in controlling, reducing and alleviating many of these disease states.

In DE10238045 there are described compounds that consist of a sulfanyl imidazole moiety that is substituted with an amino pyridine and a substituted phenyl group. The sulfanyl group is exemplified as being methylsulfanyl or benzylsulfanyl.

SUMMARY OF THE INVENTION

In one aspect, the invention provides a compound of the following structure:

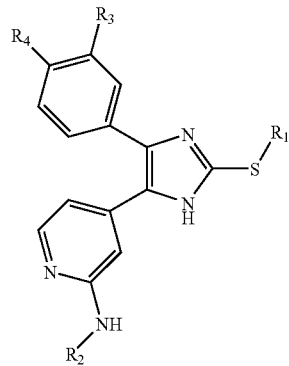

(Formula I)

in which
$R_1$=2-hydroxypropyl;
  3-hydroxypropyl;
  2-hydroxyethyl;
  2,3-dihydroxypropyl;
  2-hydroxy-3-aminopropyl;
  2-hydroxy-3-aminobutyl;
  3,4-dihydroxybutyl;
  2,3,4-trihydroxybutyl;
  —$(CH_2)_n$—COR, in which R=OH, O-alkyl ($C_1$-$C_4$), O-alkylaryl, $NH_2$, NHMe, or NHOH, and n=1, 2, 3, 4, 5;
  —$CH_2$—P=O(OR)$_2$ in which R=H, $CH_3$, or $CH_2CH_3$;
  —$CH_2$—$(CH_2)_m$—S(=O)$_n$—R, in which R=alkyl ($C_1$-$C_5$), OH, $NH_2$, and m 1, 2, 3 and n=0, 1, 2;
  Glycidyl;
  3-methylglycidyl;
  —$CH_2$—CHOH—COR, in which R=OH, OMe, OEt, $NH_2$, or NHOH;
  —CH($CH_2OH$)—COR, in which R=OH, OMe, OEt, $NH_2$, or NHOH;
  —$CH_2$—CHOH—CN; or
  —CH($CH_2OH$)—CN;
$R_2$=methyl;
  ethyl;
  isopropyl;
  sec-butyl;
  isobutyl;
  2-(3-methyl)butyl;
  cyclopropyl;
  cyclobutyl;
  cyclopentyl;
  cyclohexyl;
  morpholinyl;
  methylcyclohexyl;
  methylcyclopentyl;
  methylmorpholinyl;
  hydroxycyclohexyl; or
  hydroxycyclopentyl;

$R_3$=H, halogen, $CF_3$, or $OCF_3$;
$R_4$=H, halogen, $CF_3$, or $OCF_3$; and
$R_5$=H, halogen, or $CF_3$; or a salt thereof.

In another aspect, the invention provides a pharmaceutical composition comprising a compound or salt of Formula I and a pharmaceutically acceptable excipient, carrier or diluent.

In certain embodiments, the invention provides a compound or salt of Formula I, or a pharmaceutical composition thereof, for use in medicine. In certain embodiments, the invention provides a compound or salt of Formula I, or a pharmaceutical composition thereof, for binding to a protein. In certain embodiments, the binding results in inhibition of the protein. In certain embodiments, the binding occurs at the ATP binding site of a protein. In certain embodiments, the protein is a kinase. In certain embodiments, the kinase is a MAP p38 kinase.

In certain embodiments, the invention provides a compound or salt of Formula I, or a pharmaceutical composition thereof, for use in the manufacture of a medicament for the inhibition of a protein.

In another aspect, the invention provides a method of inhibiting a protein, the method comprising administering an inhibitory amount of a compound or salt of Formula I, or a pharmaceutical composition thereof, to a patient in need thereof.

In certain aspects and embodiments described herein, the binding occurs in vitro or in vivo.

In another aspect, this invention features a method for treating an inflammatory, viral, bacterial, cardiovascular modulators, metabolic or immune disorder. The method includes administering to a subject in need thereof an effective amount of a compound described herein (e.g., a compound or salt of Formula I, or a pharmaceutical composition thereof).

In another aspect, the invention provides a method of treating Alzheimer's disease, stroke, diabetes, obesity, inflammation, or cancer. The method comprises administering a compound or salt of Formula I, or a pharmaceutical composition thereof, to a patient in need thereof.

In another aspect, the invention provides a compound or salt of Formula I, or a pharmaceutical composition thereof, for the treatment of an inflammatory disorder. In another aspect, the invention provides a method of treating an inflammatory disorder, comprising administering a therapeutically effective amount of a compound or salt of Formula I, or a pharmaceutical composition thereof, to a patient in need thereof.

In certain embodiments, the inflammatory disorder is a chronic inflammation. In certain embodiments, the inflammatory disorder is an inflammatory bowel disease. In certain embodiments, the inflammatory bowel disease is Crohn's disease, ulcerative colitis, collagenous colitis, lymphocytic colitis, ischaemic colitis, diversion colitis, Behcet's syndrome, infective colitis or indeterminate colitis.

In certain embodiments, the inflammatory disorder is psoriasis. In certain embodiments, the psoriasis is plaque psoriasis, pustular psoriasis, guttate psoriasis, psoriatic arthritis, inverse psoriasis or erythrodermic psoriasis.

In certain embodiments, the inflammatory disorder is sarcoidosis, rheumatoid arthritis, asthma, chronic obstructive pulmonary disease, or atherosclerosis.

DETAILED DESCRIPTION

The present invention relates to compounds of the following structure (Formula I) and uses thereof:

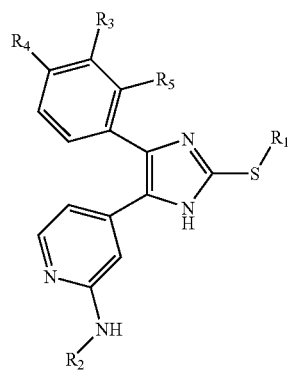

Formula I wherein
$R_1$=2-hydroxypropyl;
  3-hydroxypropyl;
  2-hydroxyethyl;
  2,3-dihydroxypropyl;
  2-hydroxy-3-aminopropyl;
  2-hydroxy-3-aminobutyl;
  3,4-dihydroxybutyl;
  2,3,4-trihydroxybutyl;
  —$(CH_2)_n$—COR, in which R=OH, O-alkyl ($C_1$-$C_4$), O-alkylaryl, $NH_2$, NHMe, or NHOH, and n=1, 2, 3, 4, 5;
  —$CH_2$—P=$O(OR)_2$ in which R=H, $CH_3$, or $CH_2CH_3$;
  —$CH_2$—$(CH_2)_m$—$S(=O)_n$—R, in which R=alkyl ($C_1$-$C_5$), OH, $NH_2$, and m=1, 2, 3 and n=0, 1, 2;
  Glycidyl;
  3-methylglycidyl;
  —$CH_2$—CHOH—COR, in which R=OH, OMe, OEt, $NH_2$, or NHOH;
  —$CH(CH_2OH)$—COR, in which R=OH, OMe, OEt, $NH_2$, or NHOH;
  —$CH_2$—CHOH—CN; or
  —$CH(CH_2OH)$—CN;
$R_2$=methyl;
  ethyl;
  isopropyl;
  sec-butyl;
  isobutyl;
  2-(3-methyl)butyl;
  cyclopropyl;
  cyclobutyl;
  cyclopentyl;
  cyclohexyl;
  morpholinyl;
  methylcyclohexyl;
  methylcyclopentyl;
  methylmorpholinyl;
  hydroxycyclohexyl; or
  hydroxycyclopentyl;
$R_3$=H, halogen, $CF_3$, or $OCF_3$;
$R_4$=H, halogen, $CF_3$, or $OCF_3$; and
$R_5$=H, halogen, or $CF_3$; or a salt thereof.

In PCT Publication No. WO2006089798 there are disclosed imidazole derivatives substituted with methylmercapto at the 2-position. Nitrogen bearing substituents at the 2-position of the pyridinyl group are according to this disclosure introduced by aromatic nucleophilic substitution as one of the final steps in the synthesis.

The compounds of the present invention can be made by following methods: N-protected N-substituted 2-aminopicolines are prepared according to Scheme 1.

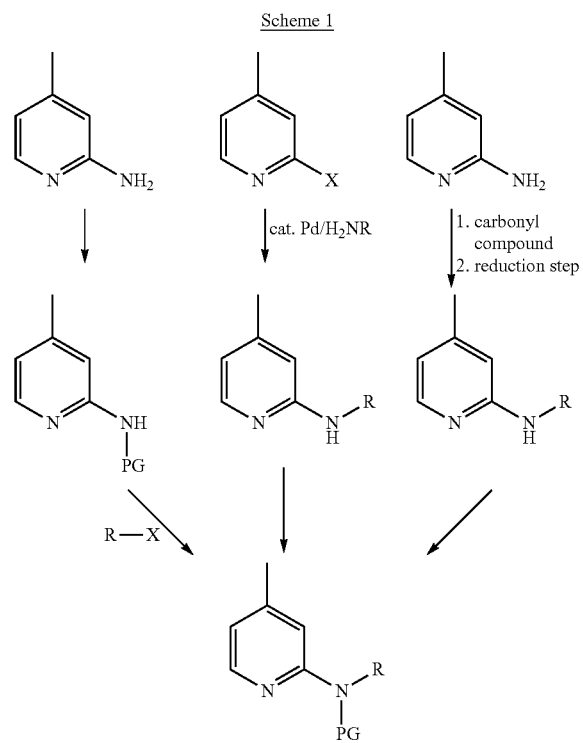

According to Variant 1, 2-aminopicoline is protected. Suitable protective groups are carbamate protective groups like benzyloxycarbonyl or t-butyloxycarbonyl (boc). The latter one is preferred. In the next step the nitrogen is alkylated by employing a suitable alkyl ting agent, a suitable base in a suitable solvent. A suitable alkyl ting agent can be an alkyl halogenated like a bromide, iodide or chloride, or an alkyl ester of an alkyl or arylsulfonic acid. Bromides and iodides are generally preferred. A suitable base can be an alkali alkoxide, an alkali alkane, an alkali hydride or an alkali hydroxide. Hydrides are generally preferred. A suitable solvent can be an ether like diethylether, THF dimethoxyethane or dioxane, or an amide like dimethylformamide (DMF), dimethylacetamide, N-methylpyrrolidone. Another inert solvent is dimethylsulfoxide (DMSO). A preferred solvent is DMF or DMSO.

According to Variant 2, a 2-substituted picoline derivative with the substituent being preferably bromo, is reacted with a primary amine under catalysis of a transition metal, preferably palladium in the presence of an inorganic base and a phosphine ligand in an inert organic solvent. The protective group is introduced in a similar manner as in Variant 1.

In Variant 3, alkylgroups are introduced by reacting 2-aminopicoline with a suitable aldehyde or ketone in a suitable solvent in the presence of a suitable acid or Lewis acid. A suitable solvent can be anhydrous methanol or ethanol, preferably dichloroethane. A suitable acid can be acetic acid, a alkyl or aryl sulfonic acid, anhydrous HCl. A suitable Lewis acid is stannous chloride, zinc chloride. A preferred Lewis acid is titanium tetraisopropoxide. After formation of the imine reduction to the amine is achieved by employing a suitable reductant. In an alcoholic solvent sodium borohydride can be used or preferably sodium cyanoborohydride. In dichloroethane the reductant of choice is sodium triacetoxyborohydride.

The secondary amine obtained by this method can be protected as in Variant 2.

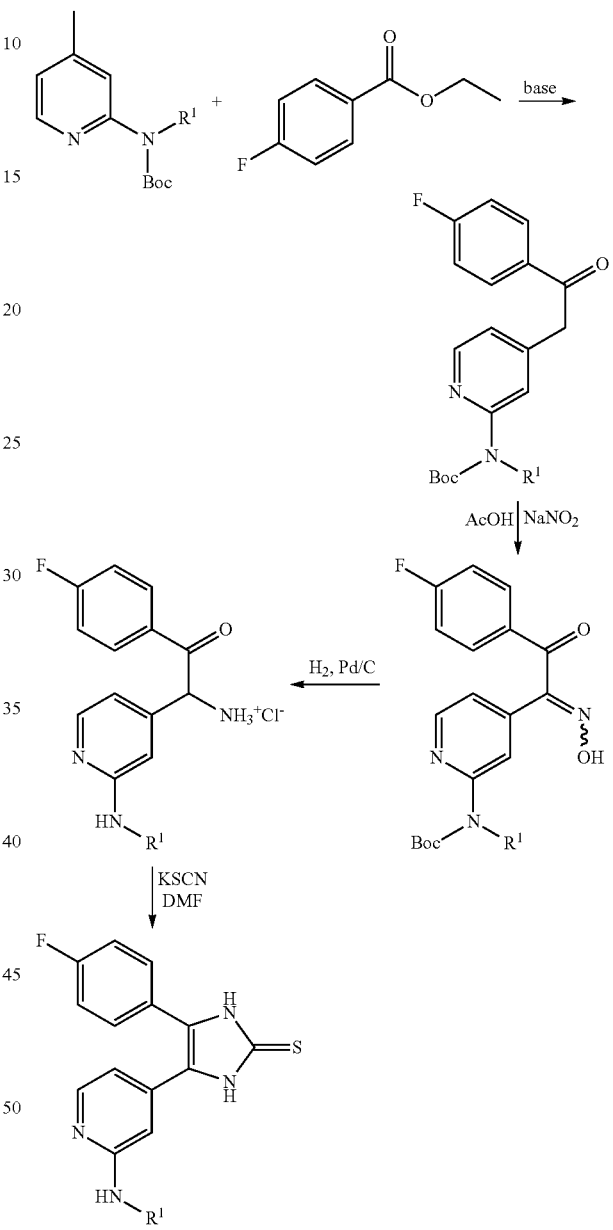

N-protected N-substituted 2-aminopicolines can be employed to form dihydroimidazolethiones (Scheme 2). This is achieved by treating suitably substituted picolines with a strong base in the presence of a suitable alkyl benzoate. The same transformation can be achieved by deprotonating picoline first and then adding the alkyl benzoate at low temperature. Suitable bases are lithium diisopropylamide, lithium hexamethyldisilazide, and sodium hexamethyldisilazide.

A preferred mode for this reaction is to add sodium hexamethyldisilazide to a mixture of the picoline and the benzoate at a temperature of −80-10° C., conveniently at 0° C. The derived ketone is transformed to an oxime ketone. This can be achieved for example by treating the ketone with a strong base like an alcoholate in the presence of an alkyl nitrite like amyl nitrite. A preferred method to obtain the desired oxime ketone consists of reacting the ketone in acetic acid in the presence of sodium nitrite or another suitable nitrite.

In the next step the oxime group has to be reduced to an amino group. This transformation can be achieved by treatment with zinc and an acid, preferably acetic acid or HCl. Preferably it is possible to use catalytic hydrogenation employing palladium on charcoal as the catalyst in the presence of HCl. Under these conditions protective groups on the aminopyridine group will also be removed, if the protective group consists of t-butoxycarbonyl (boc) or benzyloxycarbonyl.

The resulting aminoketone is in the next step reacted with an inorganic thiocyanate like sodium, potassium or ammonium thiocyanate. The reaction can be conducted in a way that the aminoketone and the thiocyanate are heated in an inert solvent like DMF or DMSO. Isolation conveniently by addition of water and collecting the product by filtration will yield the thione.

Scheme 3

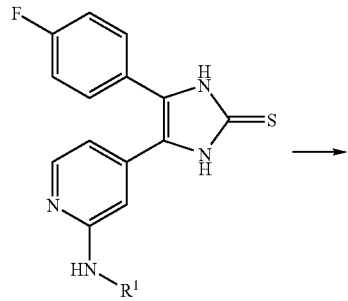

-continued

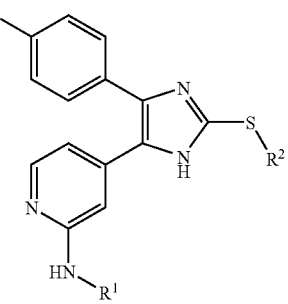

Alkylation of the sulfur in thiones as in Scheme 3 can be achieved by employing a variety of suitable alkylating agents. Among these there are alkyl halogenides, esters of alkyl and aryl sulfonic acids, epoxides and aziridines. Characteristic for the present invention is carrying out this alkylation reaction with alkylating agent that carry polar functional groups or groups from which these polar functional groups can be liberated or from which they can be formed. Polar groups in this context are hydroxy, amino, carboxy, phosphonate, sulfonate, sulfonamide, sulfoxide, sulfone, carboxamide, and carboxyhydroxymate. These groups may appear alone or in combination with other polar groups as listed above.

Alternatively it is possible to construct substituted imidazoles of Formula I as depicted in Schemes 4 and 5.

According to these Schemes, condensing 2-fluoropicoline with a methyl or ethyl benzoate generates a ketone that is then transformed to the oxime ketone with following reduction to the aminoketone similar as shown in Scheme 2.

Scheme 4

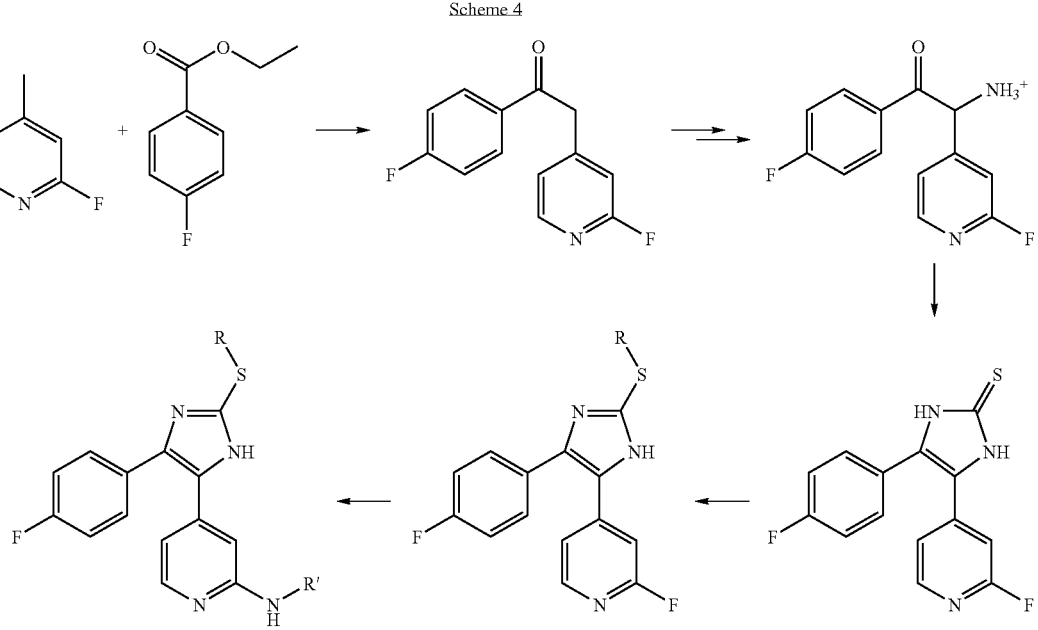

Scheme 5

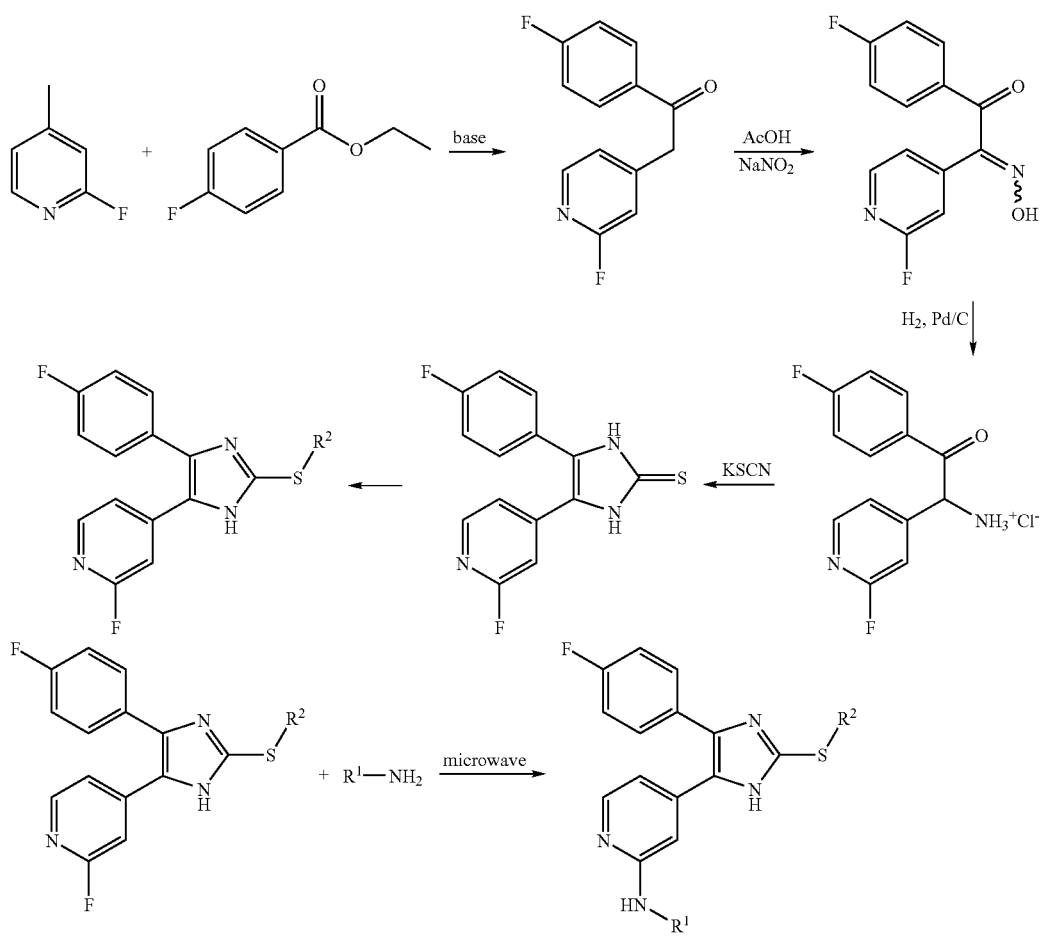

Reaction with a thiocyanate as in Scheme 2 will generate a thione that will undergo alkylation with an alkylating agent, examples of which can be found above. In the final step the fluorine will be displaced by an amine, preferably a primary amine. This reaction can take place in a suitable solvent with high boiling point as for example DMF, NMP, DMSO, diethyleneglycol, or by heating the fluoropyridine in an excess of the amine. The last variant can be preferably carried out in a microwave oven.

The invention also provides methods of treating an inflammatory, viral, bacterial, cardiovascular modulators, metabolic or immune disorder. The methods include administering to a subject in need thereof an effective amount of a compound described herein (e.g., a compound or salt of Formula I, or a pharmaceutical composition thereof).

In another aspect, the invention provides a method of treating Alzheimer's disease, stroke, diabetes, obesity, inflammation, or cancer. The method comprises administering a compound or salt of Formula I, or a pharmaceutical composition thereof, to a patient in need thereof.

In another aspect, the invention provides a compound or salt of Formula I, or a pharmaceutical composition thereof, for the treatment of an inflammatory disorder. In another aspect, the invention provides a method of treating an inflammatory disorder, comprising administering a therapeutically effective amount of a compound or salt of Formula I, or a pharmaceutical composition thereof, to a patient in need thereof.

In certain embodiments, the inflammatory disorder is a chronic inflammation. In certain embodiments, the inflammatory disorder is an inflammatory bowel disease. In certain embodiments, the inflammatory bowel disease is Crohn's disease, ulcerative colitis, collagenous colitis, lymphocytic colitis, ischaemic colitis, diversion colitis, Behcet's syndrome, infective colitis or indeterminate colitis.

In certain embodiments, the inflammatory disorder is psoriasis. In certain embodiments, the psoriasis is plaque psoriasis, pustular psoriasis, guttate psoriasis, psoriatic arthritis, inverse psoriasis or erythrodermic psoriasis.

In certain embodiments, the inflammatory disorder is sarcoidosis, rheumatoid arthritis, asthma, chronic obstructive pulmonary disease, or atherosclerosis.

To practice a method of treating a disease, the compounds of this invention can be administered to a patient, for example, in order to treat a disease described herein. The compound can, for example, be administered in a pharmaceutically acceptable carrier such as physiological saline, in combination with other therapeutic agents, and/or together with appropriate excipients. The compound described herein can, for example, be administered by injection, intravenously, intraarterially, subdermally, intraperitoneally, intramuscularly, or subcutaneously; or orally, buccally, nasally, transmucosally, topically, in an ophthalmic preparation, by inhalation, by intracranial injection or infusion techniques, with a dosage ranging from about 0.05 to about 20 mg/kg of body weight, preferably dosages between 5 mg and 1000 mg/dose, every 4 to 120 hours, or according to the requirements of the particular therapeutic agent. The methods herein contemplate administration of an effective amount of compound or compound composition to achieve the desired or stated effect. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, therapeutic agent combination, the severity and course of the disease, condition or symptoms, the patient's disposition to the disease, condition or symptoms, and the judgment of the treating physician.

Pharmaceutical compositions of this invention comprise a compound of this invention or a pharmaceutically acceptable salt thereof; and any pharmaceutically acceptable carrier, adjuvant or vehicle. Such compositions may optionally comprise additional therapeutic agents. The compositions delineated herein include the compounds of the formulae delineated herein, as well as additional therapeutic agents if present, in amounts effective for achieving a modulation of a disease.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying therapeutic agent delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein. Oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient that is solid at room temperature but liquid at the rectal temperature and therefore will melt in the rectum to release the active components. Such materials include, but are not limited to, cocoa butter, beeswax and polyethylene glycols.

DEFINITIONS

"The term "cyclic" refers to a hydrocarbon cyclic ring including fully saturated, partially saturated, and unsaturated mono-, bi, and tri-cyclic rings having 3 to 34 ring atoms, preferably, 3-8 ring atoms. The term "heterocyclic" refers to a hydrocarbon cyclic ring including fully saturated, partially saturated, and unsaturated mono-, bi, and tri-cyclic rings having 4 to 34 ring atoms, preferably, 4 to 8, ring atoms having one or more heteroatoms, such as S, O, or N in each ring.

The terms "halogen" and "halo" refer to radicals of fluorine, chlorine, bromine or iodine.

The term "alkyl" (or "alkenyl" or "alkynyl") refers to a hydrocarbon chain that may be a straight chain or branched chain, containing the indicated number of carbon atoms. For example, C1-C10 indicates that the group may have from 1 to 10 (inclusive) carbon atoms in it. Alkenyl groups and alkynyl groups have one or more double or triple carbon-carbon bonds, respectively, in the chain.

The term "aryl" refers to a hydrocarbon ring system (monocyclic or bicyclic) having the indicated number of carbon atoms and at least one aromatic ring. Examples of aryl moieties include, but are not limited to, phenyl, naphthyl, and pyrenyl.

The term "heteroaryl" refers to a ring system (monocyclic or bicyclic) having the indicated number of ring atoms including carbon atoms and at least one aromatic ring. The ring system includes at least one heteroatom such as O, N, or S (e.g., between 1 and 4 heteroatoms, inclusive, per ring) as part of the ring system. Examples of heteroaryl moieties include, but are not limited to, pyridyl, furyl or furanyl, imidazolyl, benzimidazolyl, pyrimidinyl, thiophenyl or thienyl, quinolinyl, indolyl, and thiazolyl.

The term "alkoxy" refers to an —O-alkyl radical.

The term "cycloalkyl" refers to a nonaromatic hydrocarbon ring system (monocyclic or bicyclic), containing the indicated number of carbon atoms.

The term "heterocycloalkyl" refers to a nonaromatic ring system (monocyclic or bicyclic), containing the indicated number of ring atoms including carbon atoms and at least one heteroatom such as O, N, or S (e.g., between 1 and 4 heteroatoms, inclusive, per ring) as part of the ring system.

The compounds described herein have a range of utilities including use as anti-inflammatory compounds, inhibitors of neuro degeneration, anti-viral compounds, anti-bacterial compounds, modulators of ion-channels, cardio-vascular modulators, metabolic modulators and immune modulators. In many instances, their utility is related, effects on cells of the macrophage type either as phagocytes or antigen presenting cells. Such an example is seen in cardiovascular diseases such as atherosclerosis where there is a strong inflammatory component to the events that result in the thickening and fragmentation of the plaque. This inflammation may be effectively reduced by the application of a range of agents that interact with the macrophage class.

The compounds described herein include the compounds themselves, as well as their salts, if applicable. Such salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as tetramethylammonium ion.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., treating a disease).

In another aspect, this invention features a method for treating an inflammatory, viral, bacterial, cardiovascular modulators, metabolic or immune disorder. The method includes administering to a subject in need thereof an effective amount of a compound described herein. Optionally, the method includes co-usage with other anti-inflammatory agents or therapeutic agents. The use of the compounds described herein improves therapy in part because of the preferential activity on targets such as p38 kinase.

The present invention also features a pharmaceutical composition including at least one compound of Formula (I) and a pharmaceutically acceptable carrier. Optionally, the pharmaceutical composition includes one or more other therapeutic agents.

Also within the scope of this invention are compositions having one or more of the compounds of Formula (I), optionally including one or more other therapeutic agent, for use in treating various diseases described above, and the use of such a composition for the manufacture of a medicament for the just-described use.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. A suitable in vitro assay can be used to preliminarily evaluate a compound of formula (I) in treating a disease. In vivo screening can also be performed by following procedures well known in the art. See the specific examples below.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

The invention will be further described in the following examples. It should be understood that these examples are for illustrative purposes only and are not to be construed as limiting this invention in any manner.

EXAMPLES tert-Butyl 4-methylpyridin-2-ylcarbamate

Example 1

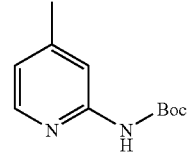

To a solution of freshly distilled tert-butanol (450 mL) and di-tert-butyl dicarbonate (16.81 g, 77.0 mmol) was added slowly 2-aminopicoline (7.57 g, 70.0 mmol). The mixture was stirred at room temperature for 3 d, the solvent was removed in vacuo and the residue was recrystallized from 2-propanol, affording 12.30 g (84%) of a colorless solid.

$^1$H-NMR (CDCl$_3$) δ 1.53 (s, 9H, C(CH$_3$)$_3$), 2.34 (s, 3H, CH$_3$), 6.75-6.78 (m, 1H, C$^5$—H Pyr), 7.85 (s, 1H, 1H, C$^3$—H Pyr), 8.17 (d, J=5.2 Hz, 1H, C$^6$—H Pyr), 9.40 (bs, 1H, NH)

IR (ATR) ṽ (cm$^{-1}$) 3178, 2975 (CH$_3$), 1720, 1612, 1574, 1530, 1422, 1390, 1365, 1291, 1257, 1230, 1154, 1120, 1059, 995, 866, 816, 766, 743

General Procedure for the Synthesis of N-Alkyl/Phenylalkyl-N-Boc-4-Methylpyrindin-2-Amines (General Procedure A)

To a solution of tert-butyl 4-methylpyridin-2-ylcarbamate 1 (1 equiv.) in dry DMF was added under an argon-atmosphere NaH (1.25 equiv., 60% oil dispersion) at 0° C. in such a manner that the temperature was kept below 5° C. The reaction mixture was kept at 0° C. for 20 min followed by the addition of the alkyl/phenylalkyl halides (1.15 equiv.) at the same temperature. After additional stirring at 0° C. for 30 min the mixture was allowed to warm to room temperature within 1 h. After stirring at room temperature for 1 h, H$_2$O and EtOAc were added. The organic layer was washed subsequently with HCl (0.1 M), sodium bicarbonate and brine, N-Boc-4-methyl-N-(1-phenylethyl)pyridin-2-amine Example 2a

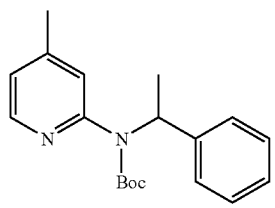

Compound 2a was prepared according to general procedure A from 1 (4.16 g, 20.0 mmol), NaH (1.00 g, 25.0 mmol, 60% oil dispersion), 1-phenylethyl bromide (4.25 g, 23.0 mmol) and DMF (60 mL).
flash chromatography: SiO$_2$, from n-hexane/EtOAc 5:1 to n-hexane/EtOAc 3:1
yield: 4.76 g (76%) of a colorless oil
$^1$H-NMR (CDCl$_3$) δ 1.22 (s, 9H, C(CH$_3$)$_3$), 1.65 (d, J=7.02 Hz, 3H, CH$_3$), 2.21 (s, 3H, CH$_3$, Pyr), 5.69-5.76 (m, 1H, CH), 6.80 (d, J=4.68 Hz, 1H, C$^5$—H Pyr), 7.08-7.25 (m, 4H, Ph), 7.36-7.40 (m, 2H, 1×Ph, C$^3$—H Pyr), 8.22 (d, H, J=5.00 Hz, C$^6$—H Pyr)
IR (ATR) ṽ (cm$^{-1}$) 2976, 1699, 1602 1560, 1497, 1478, 1450, 1401, 1366, 1320, 1271, 1249, 1152, 1116, 1095, 872, 773 (Ar), 696 (Ar)

N-Benzyl-N-boc-4-methylpyridin-2-amine

Example 2b

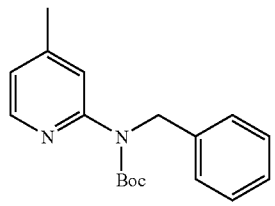

Compound 2b was prepared according to general procedure A from 1 (0.75 g, 3.6 mmol), NaH (0.18 g, 4.5 mmol), benzyl bromide (0.71 g, 4.1 mmol, 60% oil dispersion) and DMF (11 mL).
flash chromatography: SiO$_2$, n-hexane/EtOAc 3:1
yield: 0.60 g (56%) as a colorless solid
$^1$H-NMR (CDCl$_3$) δ 1.42 (s, 9H, C(CH$_3$)$_3$), 2.32 (s, 3H, CH$_3$), 5.22 (s, 2H, CH$_2$), 6.79-6.83 (m, 1H, C$^5$—H Pyr), 7.18-7.32 (m, 5H, Ph), 7.56 (s, 1H, C$^3$—H Pyr), 8.23 (d, J=5.06 Hz, 1H, C$^5$—H Pyr)
IR (ATR) ṽ (cm$^{-1}$) 2984, 1717, 1603 1508, 1368, 1304, 1269, 1237, 1153, 1105, 1090, 1015, 853, 812, 766 (Ar), 687 (Ar)

N-Boc-N-isobutyl-4-methylpyridin-2-amine

Example 2c

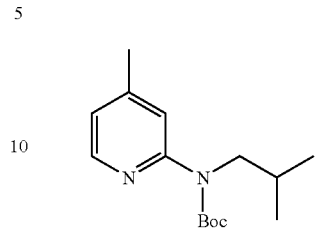

Compound 2c was prepared according to general procedure A from 1 (2.08 g, 10.0 mmol), NaH (0.50 g, 12.5 mmol, 60% oil dispersion), isobutyl bromide (1.55 g, 11.3 mmol) and DMF (20 mL).
flash chromatography: SiO$_2$, from n-hexane/EtOAc 5:1 to n-hexane/EtOAc 3:1
yield: 1.62 g (61%) of a colorless oil
$^1$H-NMR (CDCl$_3$) δ 0.80 (d, J=6.71 Hz, 6H, 2×CH$_3$), 1.44 (s, 9H, C(CH$_3$)$_3$), 1.70-1.90 (m, 1H, CH), 2.28 (s, 3H, CH$_3$, Pyr) 3.76 (d, J=7.33 Hz, 2H, CH$_2$), 6.78-6.81 (m, 1H, C$^5$—H Pyr), 7.31 (s, 1H, C$^3$—H-Pyr), 8.18 (d, J=5.06 Hz, C$^6$—H Pyr)
IR (ATR) ṽ (cm$^{-1}$) 2961, 2872, 1702, 1603, 1562, 1479, 1454, 1381, 1366, 1277, 1245, 1143, 1048, 991, 883, 818, 770

N-Boc-N-ethyl-4-methylpyridin-2-amine

Example 2d

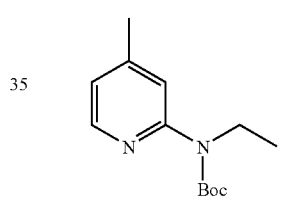

Compound 2d was prepared according to general procedure A from 1 (4.16 g, 20 mmol), NaH (1.00 g, 25.0 mmol, 60% oil dispersion), ethyl bromide (2.47 g, 22.7 mmol) and DMF (60 mL).
flash chromatography: SiO$_2$, petroleum ether/EtOAc 5:1
yield: 3.6 g (76%) of a colorless oil
$^1$H-NMR (CDCl$_3$) δ 1.03 (t, J=6.96 Hz, 3H, CH$_3$), 1.33 (s, 9H, C(CH$_3$)$_3$), 2.11 (s, 3H, CH$_3$, Pyr), 3.78 (q, J=6.97 Hz, 2H, CH$_2$), 6.59-6.62 (m, 1H, C$^5$—H Pyr), 7.28 (s, 1H, C$_3$—H Pyr), 8.01-8.03 (m, 1H, C$^6$—H Pyr)
IR (ATR) ṽ (cm$^{-1}$) 2976 (—CH$_3$), 2932, 1702, 1603, 1564, 1477, 1448 (—CH$_3$), 1411, 1387, 1366, 1316, 1272, 1252, 1178, 1143, 1118, 1104, 1084, 990, 875, 815, 771, 747

N-Boc-N,4-dimethylpyridin-2-amine

Example 2e

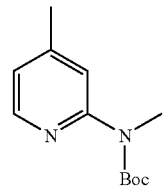

Compound 2e was prepared according to general procedure A from 1 (2.00 g, 9.6 mmol), NaH (0.48 g, 12.0 mmol, 60% oil dispersion), methyl iodide (1.56 g, 11.0 mmol) and DMF (20 mL).
flash chromatography: SiO$_2$, from n-hexane/EtOAc 5:1 to n-hexane/EtOAc 3:1
yield: 1.42 g (67%)
$^1$H-NMR (CDCl$_3$) δ 1.35 (s, 9H, C(CH$_3$)$_3$), 2.14 (s, 3H, CH$_3$, Pyr), 3.21 (s, 3H, CH$_3$), 6.42-6.47 (m, 1H, C$^5$—H Pyr), 7.35 (s, 1H, C$^3$—H Pyr), 8.03-8.05 (m, 1H, C$^6$—H Pyr)
IR (ATR) ṽ (cm$^{-1}$) 2977 (—CH$_3$), 1703, 1604, 1561, 1480, 1399, 1349, 1280, 1254, 1143, 1116, 1099, 989, 882, 818, 770, 748

General Procedure for the Synthesis of N-Alkyl-4-Methylpyrindin-2-Amines Via Buchwald-Hartwig-Reaction (General Procedure B)

2-Bromo-4-methylpyridine (1.0 equiv.), amine (1.2 equiv.) or corresponding hydrochlorides (1.2 equiv.), NaOt-Bu (1.4 equiv., or in case of hydrochlorides 2.4 equiv.), Pd$_2$(dba)$_3$ (0.02 equiv.), BINAP (0.04 equiv.) were dissolved in dry toluene under argon atmosphere. The mixture was heated to 70° C. or to reflux until the disappearance of the starting material 2-bromo-4-methylpyridine (TLC-control: n-hexane/EtOAc 3:1 or 1:1). The mixture was allowed to cool to room temperature before n-hexane was added. The formed precipitate was filtered off and the filtrate concentrated to dryness. Once again, n-hexane was added to the residue and the precipitate was filtered off. The filtrate was concentrated in vacuo. The crude product was used in the next reaction (except compound 3d which was purified by flash chromatography).

4-Methyl-N-(3-methylbutan-2-yl)pyridin-2-amine

Example 3a

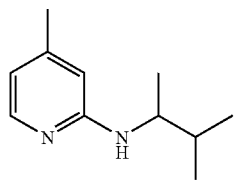

Compound 3a was prepared according to general procedure B from 2-bromo-4-methylpyridine (1.37 g, 8.0 mmol), 3-methyl-2-butylamine (0.83 g, 9.6 mmol), NaOt-Bu (1.07 g, 11.2 mmol), Pd$_2$(dba)$_3$ (0.14 g, 0.16 mmol), BINAP (0.20 g, 0.32 mmol), and toluene (30 mL) within 3 h at 70° C.
yield: 1.2 g (crude product)

N-sec-Butyl-4-methylpyridin-2-amine

Example 3b

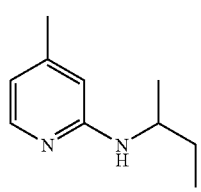

Compound 3b was prepared according to general procedure B from 2-bromo-4-methylpyridine (1.00 g, 5.8 mmol), sec-butylamine (0.51 g, 7.0 mmol), NaOt-Bu (0.78 g, 8.1 mmol), Pd$_2$(dba)$_3$ (107 mg, 0.12 mmol), BINAP (145 mg 0.23 mmol), and toluene (30 mL) within 2 h at 70° C.
yield: 1.1 g (crude product)

N-Isopropyl-4-methylpyridin-2-amine

Example 3c

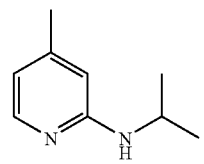

Compound 3c was prepared according to general procedure B from 2-bromo-4-methylpyridine (2.00 g, 11.6 mmol), isopropylamine (0.83 g, 13.9 mmol), NaOt-Bu (1.56 g, 16.2 mmol), Pd$_2$(dba)$_3$ (0.20 g, 0.23 mmol), BINAP (0.29 g, 0.47 mmol), and toluene (40 mL) refluxing for 50 min.
yield: 1.37 g (crude product)

4-Methyl-N-(tetrahydro-2H-pyran-4-yl)pyridin-2-amine

Example 3d

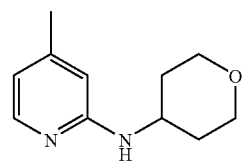

Compound 3d was prepared according to general procedure B from 2-bromo-4-methylpyridine (0.20 g, 1.2 mmol), tetrahydro-2H-pyran-4-amine hydrochloride (0.19 g, 1.4 mmol), NaOt-Bu (0.27 g, 2.8 mmol), Pd$_2$(dba)$_3$ (21 mg, 0.023 mmol), BINAP (29 mg, 0.046 mmol), and toluene (30 mL) within 2 h at 70° C.
flash chromatography: SiO$_2$, from n-hexane/EtOAc 1:1 to 100% EtOAc
yield: 0.11 g (49%)

General Procedure for the Synthesis of N-Alkyl-N-Boc-4-Methylpyridin-2-Amines Via Boc-Protection (General Procedure C)

N-Alkyl-4-methylpyridin-2-amine 3 (1.0 equiv.) was dissolved in dry DCM and subsequently treated with di-tert-butyl dicarbonate (2.5 equiv.) and DMAP (catalytic amounts). The reaction mixture was stirred for 16 h at room temperature and the solvent was removed in vacuo. n-Hexane was added to the residue, the precipitate was filtered off, and the filtrate was concentrated under reduced pressure. The residue was purified by flash chromatography.

N-Boc-4-methyl-N-(3-methylbutan-2-yl)pyridin-2-amine

Example 2f

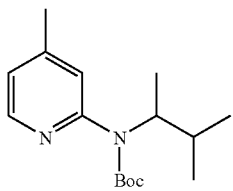

Compound 2f was prepared according to general procedure C from 3a (1.20 g), di-tert-butyl dicarbonate (3.67 g, 16.8 mmol) and DCM (80 mL).

flash chromatography: SiO$_2$, n-hexane/EtOAc 5:1 to 3:1 yield: 1.40 g (63%, covering two steps) of a colorless oil $^1$H-NMR (CDCl$_3$) δ 0.86 (d, J=6.68 Hz, 3H, CH$_3$), 0.94 (d, J=6.63 Hz, 3H, CH$_3$), 1.26 (d, J=6.85 Hz, 3H, CH$_3$), 1.40 (s, 9H, C(CH$_3$)$_3$), 2.01-2.15 (m, 1H, CH), 2.28 (s, 3H, CH$_3$, Pyr) 3.82-3.97 (m, 1H, CH), 6.85 (d, J=4.73 Hz, 1H, C$^5$—H Pyr), 7.03 (s, 1H, C$^3$—H Pyr), 8.23 (d, J=5.03 Hz, 1H, C$^6$—H Pyr)

IR (ATR) v (cm$^{-1}$) 2972, 2873, 1698, 1603, 1560, 1477, 1454, 1417, 1390, 1366, 1326, 1313, 1250, 1169, 1147, 1119, 1093, 1048, 1014, 813, 770

N-Boc-4-methyl-N-(sec-butyl)pyridin-2-amine

Example 2g

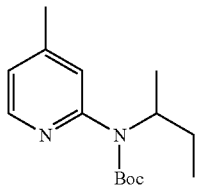

Compound 2g was prepared according to general procedure C from 3b (1.10 g), di-tert-butyl dicarbonate (3.23 g, 14.8 mmol) and DCM (30 mL).

flash chromatography: SiO$_2$, from n-hexane/EtOAc 5, 5:1 to n-hexane/EtOAc 3:1 yield: 0.94 g (61%, covering two steps) of a yellowish oil.

$^1$H-NMR (CDCl$_3$) δ 0.82-0.89 (m, 3H, CH$_3$), 1.18 (d, J=6.83 Hz, 3H, CH$_3$), 1.36-1.79 (m, 11H, C(CH$_3$)$_3$+CH$_2$), 2.27 (s, 3H, CH$_3$, Pyr) 4.11-4.22 (m, 1H, CH), 6.87 (dd, J$_1$=5.05 Hz, J$_2$=0.56 Hz, 1H, C$^5$—H Pyr), 6.96 (s, 1H, C$^3$—H Pyr), 8.23 (d, J=5.03 Hz, 1H, C$^6$—H Pyr)

IR (ATR) v (cm$^{-1}$) 2972, 2933, 2877, 1698, 1604, 1559, 1477, 1454, 1419, 1390, 1366, 1328, 1280, 1249, 1168, 1144, 1117, 1085, 993, 883, 770

N-Boc-4-methyl-N-isopropylpyridin-2-amine

Example 2h

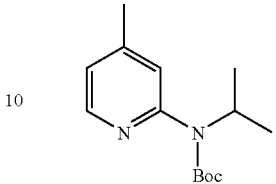

Compound 2h was prepared according to general procedure C from 3c (1.37 g), di-tert-butyl dicarbonate (3.98 g, 18.2 mmol) and DCM (100 mL).

flash chromatography: SiO$_2$, from n-hexane/EtOAc 4:1 to n-hexane/EtOAc 2:1 yield: 0.84 g (29%, covering two steps) of a colourless solid $^1$H-NMR (CDCl$_3$) δ 1.25 (dd, J$_1$=6.81 Hz, J$_2$=2.36, 6H, 2×CH$_3$), 1.43 (s, 9H, C(CH$_3$)$_3$), 2.36 (s, 3H, CH$_3$, Pyr) 4.41-4.55 (m, 1H, CH), 6.97-7.02 (m, 2H, C$^3$—/C$^5$—H Pyr), 8.34 (d, J=5.11 Hz, 1H, C$^6$—H Pyr)

IR (ATR) ṽ (cm$^{-1}$) 2975 (—CH$_3$), 1684, 1597, 1555, 1477, 1422, 1388, 1367, 1337, 1282, 1257, 1169, 1091, 988, 904, 850, 767, 747

N-Boc-4-methyl-N-(tetrahydro-2H-pyran-4-yl)pyridin-2-amine

Example 2i

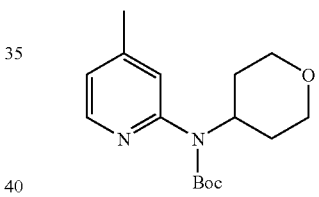

Compound 2i was prepared according to general procedure C from 3d (0.11 g, 0.57 mmol), di-tert-butyl dicarbonate (0.31 g, 1.4 mmol) and DCM (5 mL).

flash chromatography: SiO$_2$, n-hexane/EtOAc 1:1 yield: 0.11 g (66%) of a colorless solid $^1$H-NMR (CDCl$_3$) δ 1.35 (s, 9H, C(CH$_3$)$_3$), 1.73-1.77 (m, 4H, 2×CH$_2$), 2.30 (s, 3H, CH$_3$, Pyr), 3.31-3.44 (m, 2H, CH$_2$), 3.87-3.99 (m, 2H, CH$_2$), 4.19-4.35 (m, 1H, CH), 6.90-6.96 (m, 2H, C$^3$—/C$^5$—H Pyr), 8.28 (d, J=4.94 Hz, 2H, C$^6$—H Pyr)

IR (ATR) ṽ (cm$^{-1}$) 2974 (—CH$_3$), 2957, 292, 2856, 2830, 1694, 1605, 1395, 1358, 1321, 1289, 1251, 1237, 1148, 1129, 1053, 877, 766

General Procedure for the Synthesis of the 2-(2-(Boc(Alkyl/Phenylalkyl)Amino)Pyridin-4-Yl)-1-(4-Fluorophenyl)Ethanones (General Procedure D)

N-Alkyl/phenylalkyl-N-boc-4-methylpyridin-2-amine (1.0 equiv.) and ethyl 4-fluorobenzoate (1.0 or 1.1 equiv.) were dissolved in dry THF under argon atmosphere. The solution was cooled to 0° C. and NaHMDS (2 equiv. 2 M in THF) was added dropwise. The mixture was allowed to stir at this temperature for 1 h and additional 2.5 h at room temperature. The reaction was quenched with saturated NH$_4$Cl solution, EtOAc was added and the mixture was extracted with water (2×). The organic layer was dried (Na$_2$SO$_4$) and concentrated in vacuo. The crude product was purified by flash chromatography.

2-(2-(Boc(1-phenylethyl)amino)pyridin-4-yl)-1-(4-fluorophenyl)ethanone

Example 4a

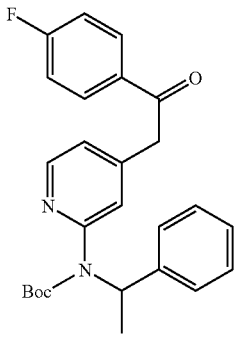

Compound 4a was prepared according to general procedure D from 2a (0.78 g, 2.5 mmol), ethyl 4-fluorobenzoate (0.42 g, 2.5 mmol), NaHMDS-solution (2.5 mL, 5.0 mmol), and THF (10 mL).
flash chromatography: $SiO_2$, n-hexane/EtOAc 3:1
yield: 0.66 g (61%) of a yellowish solid
$^1$H-NMR (CDCl$_3$) δ 1.24 (s, 9H, C(CH$_3$)$_3$), 1.69 (d, J=7.06 Hz, 3H, CH$_3$), 4.21 (s, 2H, CH$_2$), 5.08 (q, J=6.97 Hz, 1H, CH), 7.08-7.29 (m, 6H), 7.37-7.40 (m, 2H, C$^3$—/C$^5$—H 4-F-Ph), 7.95-8.02 (m, 2H, C$^2$—/C$^6$—H 4-F-Ph), 8.37 (d, J=5.08 Hz, 1H, C$^6$—H-Pyr)
IR (ATR) ṽ (cm$^{-1}$) 2972, 1702, 1691 (C=O), 1601, 1593, 1563, 1501, 1479, 1403, 1366, 1324, 1271, 1251, 1221 (C—F), 1206, 1149, 1119, 1093, 997, 982, 833 (Ar), 785, 699 (Ar)

2-(2-(1-Benzyl(boc)amino)pyridin-4-yl)-1-(4-fluorophenyl)ethanone

Example 4b

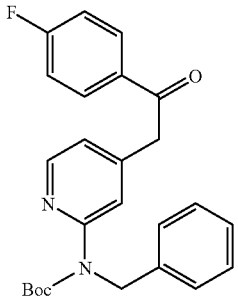

Compound 4b was prepared according to general procedure D from 2b (6.27 g, 21.0 mmol), ethyl 4-fluorobenzoate (3.89 g, 23.1 mmol), NaHMDS-solution (21.0 mL, 42.0 mmol), and THF (60 mL).
flash chromatography: $SiO_2$, from petroleum ether/EtOAc 5:1 to petroleum ether/EtOAc 3:1
yield: 5.40 g (61%) of a colorless solid.
$^1$H-NMR (CDCl$_3$) δ 1.39 (s, 9H, C(CH$_3$)$_3$), 4.25 (s, 2H, CH$_2$), 5.21 (s, 2H, CH$_2$), 6.91 (d, J=5.12 Hz, 1H, C$^5$—H Pyr), 7.01-7.29 (m, 7H, Ph+C$^3$—/C$^5$—H 4-F-Ph), 7.69 (s, 1H, C$^3$—H Pyr), 7.98-8.05 (m, 2H, C$^2$—/C$^6$—H 4-F-Ph), 8.32 (d, J=5.12 Hz, H, C$^6$—H Pyr)
IR (ATR) ṽ (cm$^{-1}$) 3074 (Ar), 3034 (Ar), 2972, 2925, 1707, 1691 (C=O), 1603, 1593, 1564, 1501, 1479, 1454, 1421, 1409, 1388, 1366, 1326, 1280, 1245, 1220 (C—F), 1204, 1159, 1145, 1116, 1075, 997, 854, 833 (Ar), 785, 743 (Ar), 732, 699 (Ar)

2-(2-(Boc(isobutyl)amino)pyridin-4-yl)-1-(4-fluorophenyl)ethanone

Example 4c

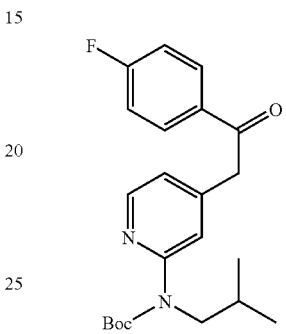

Compound 4c was prepared according to general procedure D from 2c (0.38 g, 1.4 mmol), ethyl 4-fluorobenzoate (0.27 g, 1.6 mmol), NaHMDS-solution (1.44 mL, 2.9 mmol), and THF (10 mL).
flash chromatography: $SiO_2$, from n-hexane/EtOAc 5:1 to n-hexane/EtOAc 3:1
yield: 0.45 g (64%) of a yellowish oil.
$^1$H-NMR (CDCl$_3$) δ 0.81 (d, J=6.68 Hz, 6H, 2×CH$_3$), 1.44 (s, 9H, C(CH$_3$)$_3$), 1.76-1.96 (m, 1H, CH), 3.79 (d, J=7.30 Hz, 2H, CH$_2$), 4.21 (s, 2H, CH$_2$), 6.88 (d, J=5.02 Hz, 1H, C$^5$—H Pyr), 7.05-7.13 (m, 2H, C$^3$/C$^5$—H 4-F-Ph), 7.48 (s, 1H, C$^3$—H Pyr), 7.94-8.07 (m, 2H, C$^2$/C$^6$—H 4-F-Ph), 8.27 (d, J=5.06 Hz, 1H, C$^6$—H Pyr)
IR (ATR) ṽ (cm$^{-1}$) 2961, 1693 (C=O), 1597, 1413, 1381, 1367, 1338, 1278, 1242 (C—F), 1210, 1144, 997, 989, 835, 819, 770

2-(2-(Boc(ethyl)amino)pyridin-4-yl)-1-(4-fluorophenyl)ethanone

Example 4d

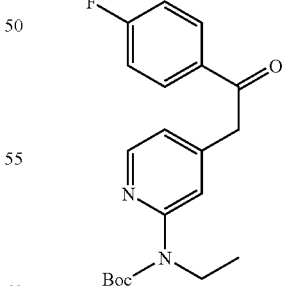

Compound 4d was prepared according to general procedure D from 2d (3.00 g, 12.7 mmol), ethyl 4-fluorobenzoate (2.35 g, 13.9 mmol), NaHMDS-solution (12.7 mL, 25.4 mmol), and THF (40 mL).
flash chromatography: $SiO_2$, from petroleum ether/EtOAc 5:1 to petroleum ether/EtOAc 3:1
yield: 3.11 g (68%) of a colorless solid.

¹H-NMR (CDCl₃) δ 1.17 (t, J=6.97 Hz, 3H, CH₃), 1.44 (s, 9H, C(CH₃)₃), 3.91 (q, J=6.97 Hz, 2H, CH₂), 4.19 (s, 2H, CH₂), 6.82-6.86 (m, 1H, C⁵—H Pyr), 7.02-7.11 (m, 2H, C³/C⁵—H 4-F-Ph), 7.56 (s, 1H, C³—H Pyr), 7.91-7.99 (m, 2H, C²/C⁶—H 4-F-Ph), 8.24 (d, J=5.04 Hz, 1H, C⁶—H Pyr)

IR (ATR) ṽ (cm⁻¹) 3083, 3003, 2978 (CH₃), 2935, 1693, 1677 (C=O), 1599, 1558, 1508, 1479, 1447 (CH₃), 1420, 1377, 1336, 1310, 1296, 1268, 1256, 1217 (C—F), 1148, 1123, 1102, 998, 968, 849, 815, 787, 759

2-(2-(Boc(methyl)amino)pyridin-4-yl)-1-(4-fluorophenyl)ethanone

Example 4e

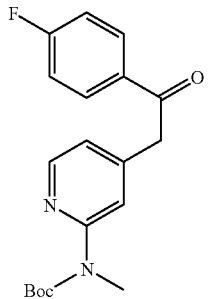

Compound 4e was prepared according to general procedure D from 2e (0.96 g, 4.3 mmol), ethyl 4-fluorobenzoate (0.80 g, 4.8 mmol), NaHMDS-solution (4.32 mL, 8.6 mmol), and THF (20 mL).
flash chromatography: SiO₂, from petroleum ether/EtOAc 5:1 to petroleum ether/EtOAc 3:1
yield: 0.96 g (64%) of a yellowish oil.
¹H-NMR (CDCl₃) δ 1.48 (s, 9H, C(CH₃)₃), 3.38 (s, 3H, CH₃), 4.23 (s, 2H, CH₂), 6.88 (dd, J₁=5.13 Hz, J₂=1.41 Hz, 1H, C⁵—H Pyr), 7.07-7.16 (m, 2H, C³/C⁵—H 4-F-Ph), 7.65 (s, 1H, C³—H Pyr), 7.96-8.03 (m, 2H, C²/C⁶—H 4-F-Ph), 8.29 (d, J=5.09 Hz, 1H, C⁶—H Pyr)

IR (ATR) ṽ (cm⁻¹) 2978 (CH₃), 1692, 1597, 1560, 1507, 1480, 1404, 1351, 1280, 1255, 1230, 1212 (C—F), 1144, 1116, 1100, 996, 987, 834, 819, 770

2-(2-(Boc(3-methylbutan-2-yl)amino)pyridin-4-yl)-1-(4-fluorophenyl)ethanone

Example 4f

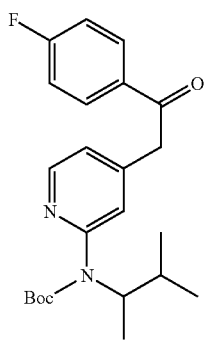

Compound 4f was prepared according to general procedure D from 2f (1.35 g, 4.8 mmol), ethyl 4-fluorobenzoate (0.92 g, 5.5 mmol), NaHMDS-solution (4.8 mL, 9.6 mmol), and THF (20 mL).
flash chromatography: SiO₂, from petroleum ether/EtOAc 5:1 to petroleum ether/EtOAc 3:1
yield: 1.15 g (60%) of a colorless oil ¹H-NMR (CDCl₃) δ 0.89 (d, J=6.7 Hz, 3H, CH₃), 0.94 (d, J₂=6.6 Hz, 3H, CH₃), 1.29 (d, J₁=10.53 Hz, J₂=6.85 Hz, 3H, CH₃), 1.41 (s, 9H, C(CH₃)₃), 2.05-2.14 (m, 1H, CH), 3.92-4.04 (m, 1H, CH), 4.24 (s, 2H, CH₂), 6.98 (dd, J₁=5.12 Hz, J₂=1.40 Hz, 1H, C⁵—H-Pyr), 7.09-7.18 (m, 3H, C³—IC₅—H-4-F-Ph+C³—H-Pyr), 7.96-8.03 (m, 2H, C²—/C⁶—H-4-F-Ph), 8.36 (d, J=5.12 Hz, 1H, C⁶—H-Pyr)

IR (ATR) ṽ (cm⁻¹) 2972, 1795, 1689 (C=O), 1598, 1557, 1507, 1477, 1412, 1390, 1367, 1327, 1235 (C—F), 1210, 1169, 1155, 1095, 1047, 998, 835, 770

2-(2-(Boc(sec-butyl)amino)pyridin-4-yl)-1-(4-fluorophenyl)ethanone

Example 4g

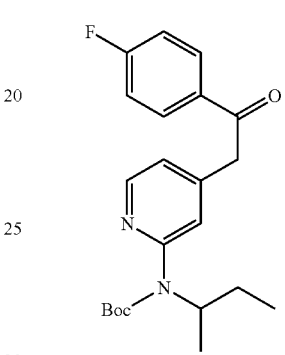

Compound 4g was prepared according to general procedure D from 2g (3.10 g, 11.7 mmol), ethyl 4-fluorobenzoate (2.15 g, 12.9 mmol), NaHMDS-solution (11.7 mL, 23.4 mmol), and THF (40 mL).
flash chromatography: SiO₂, from n-hexane/EtOAc 5:1 to n-hexane/EtOAc 3:1
yield: 2.6 g (57%) of a yellowish oil
¹H-NMR (CDCl₃) δ 0.89 (t, J=7.40 Hz, 3H, CH₃), 1.23 (d, J=6.83 Hz, 3H, CH₃), 1.36 (s, 9H, C(CH₃)₃), 1.41-1.84 (m, 2H, CH₂), 4.15-4.29 (m, 3H, CH+CH₂), 7.00 (dd, J₁=5.12 Hz, J₂=1.56 Hz, 1H, C⁵—H-Pyr), 7.08-7.17 (m, 3H, C³—/C—H-4-F-Ph+C³—H-Pyr), 7.96-8.03 (m, 2H, C²—/C⁶—H-4-F-Ph), 8.35 (d, J₁=5.10 Hz, J₂=0.58 Hz, 1H, C⁶—H-Pyr)

IR (ATR) ṽ (cm⁻¹) 2972, 2933, 2877, 1687 (C=O), 1598, 1557, 1507, 1477, 1422, 1390, 1367, 1330, 1281, 1235 (C—F), 1211, 1157, 1144, 1117, 1087, 997, 835, 770

2-(2-(Boc(isopropyl)amino)pyridin-4-yl)-1-(4-fluorophenyl)ethanone

Example 4h

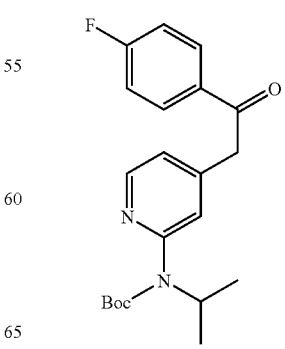

Compound 4h was prepared according to general procedure D from 2h (0.80 g, 3.2 mmol), ethyl 4-fluorobenzoate (0.54 g, 3.2 mmol), NaHMDS-solution (3.2 mL, 6.4 mmol), and THF (10 mL).

flash chromatography: SiO$_2$, from n-hexane/EtOAc 4:1 to n-hexane/EtOAc 7:3 yield: 0.82 g (69%) of a colorless solid.

$^1$H-NMR (CDCl$_3$) δ 1.09 (d, J=6.80 Hz, 6H, 2×CH$_3$), 1.24 (s, 9H, C(CH$_3$)$_3$), 4.12 (s, 2H, CH$_2$), 4.31-4.44 (m, 1H, CH), 6.88-7.01 (m, 4H, C$^3$/C$^5$—H-Pyr+C$^3$—/C$^5$—H-4-F-Ph), 7.83-7.90 (m, 2H, C$^2$—/C$^6$—H-4-F-Ph), 8.23 (d, J=5.05 Hz, 1H, C$^6$—H-Pyr)

IR (ATR) $\tilde{v}$ (cm$^{-1}$) 2976 (—CH$_3$), 1689, 1672 (C=O), 1602, 1558, 1507, 1421, 1389, 1368, 1335, 1280, 1215, 1156, 1090, 998, 909, 847, 770

2-(2-(Boc(tetrahydro-2H-pyran-4-yl)amino)pyridin-4-yl)-1-(4-fluorophenyl)ethanone Example 4i

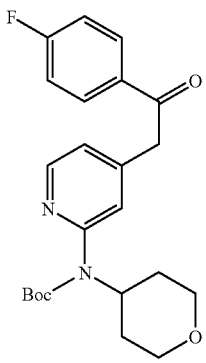

Compound 4i was prepared according to general procedure D from 2i (3.60 g, 12.6 mmol), ethyl 4-fluorobenzoate (2.34 g, 13.9 mmol), NaHMDS-solution (12.7 mL, 25.4 mmol), and THF (50 mL).

flash chromatography: SiO$_2$, from n-hexane/EtOAc 6:4 to n-hexane/EtOAc 4:6 yield: 3.7 g (69%) of a colorless solid.

$^1$H-NMR (CDCl$_3$) δ 1.36 (s, 9H, C(CH$_3$)$_3$), 1.76-1.89 (m, 4H, 2×CH$_2$), 3.35-3.48 (m, 2H, CH$_2$), 4.26-4.34 (m, 3H, CH$_2$+CH), 7.06-7.20 (m, 4H, C$^3$/C$^5$—H-Pyr+C$^3$—/C$^5$—H-4-F-Ph), 7.97-8.04 (m, 2H, C$^2$—/C$^6$—H-4-F-Ph), 8.42 (d, J=5.05 Hz, 1H, C$^6$—H-Pyr)

IR (ATR) $\tilde{v}$ (cm$^{-1}$) 2958, 2927 (—CH$_2$), 2850 (—CH$_2$), 1699, 1680 (C=O), 1593, 1557, 1506, 1420, 1377, 1366, 1352, 1323, 1298, 1260, 1223 (C—F), 1212, 1172, 1143, 1131, 1087, 1056, 1010, 999, 856, 837 (Ar), 819, 764

General Procedure for the Preparation of 2-(2-(Boc(Alkyl/Phenylalkyl)Amino)Pyridin-4-Yl)-1-(4-Fluorophenyl)Ethan-1,2-Dion-2-Oximes (General Procedure E)

A solution of 1-(4-fluorophenyl)-2-(2-(alkyl/phenylalkyl(boc)amino)pyridin-4-yl)ethanone (1.0 equiv.) in glacial acetic acid was cooled to 10° C. and a solution of NaNO$_2$ (3.0 equiv. in water (only as much water as was necessary to obtain a clear solution) was added dropwise. The reaction was allowed to warm to room temperature while stirring for 2.5 h. Water and EtOAc were added and the mixture was extracted with sodium bicarbonate several times. The organic phase was dried (Na$_2$SO$_4$) and concentrated in vacuo. After drying at the oil pump the oximes were obtained as foams which were used without purification for the next reaction.

2-(2-(Boc(1-phenylethyl)amino)pyridin-4-yl)-1-(4-fluorophenyl)ethan-1,2-dion-2-oxime Example 5a

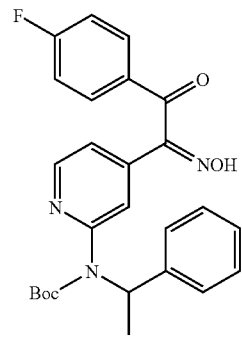

Compound 5a was prepared according to general procedure E from 4a (0.96 g, 2.2 mmol), NaNO$_2$ (0.46 g, 6.6 mmol in 5 mL water), and glacial acetic acid (15 mL).

flash chromatography: SiO$_2$, n-hexane/EtOAc 3:1 yield: 0.92 g (90%)

2-(2-(1-Benzyl(boc)amino)pyridin-4-yl)-1-(4-fluorophenyl)-ethan-1,2-dion-2-oxime Example 5b

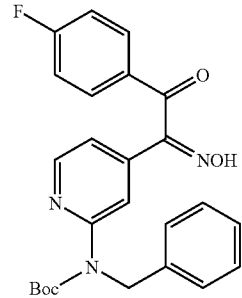

Compound 5b was prepared according to general procedure E from 4b (0.95 g, 2.2 mmol), NaNO$_2$ (0.45 g, 6.6 mmol in 5 ml water), and glacial acetic acid (15 mL).

flash chromatography: SiO$_2$, n-hexane/EtOAc 3:1 yield: 0.79 g (80%)

IR (ATR) $\tilde{v}$ (cm$^{-1}$) 2974, 1714, 1679 (C=O), 1597, 1556, 1506, 1452, 1412, 1375, 1326, 1300, 1274, 1232 (C—F), 1121, 1075, 1054, 997, 975, 948, 928, 889, 855, 832 (Ar), 810, 770, 750, 730, 700, 670

2-(2-(Boc(isobutyl)amino)pyridin-4-yl)-1-(4-fluorophenyl)ethan-1,2-dion-2-oxime

Example 5c

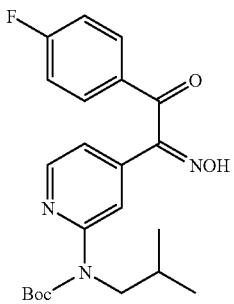

Compound 5c was prepared according to general procedure E from 4c (4.86 g, 12.7 mmol), NaNO$_2$ (2.62 g, 38.0 mmol in 30 ml water), and glacial acetic acid (60 mL).
yield: 3.90 g (crude product)

2-(2-(Boc(ethyl)amino)pyridin-4-yl)-1-(4-fluorophenyl)ethan-1,2-dion-2-oxime

Example 5d

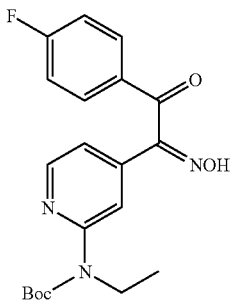

Compound 5d was prepared according to general procedure E from 4d (2.80 g, 7.8 mmol), NaNO$_2$ (1.62 g, 23.4 mmol in 15 mL water), and glacial acetic acid (50 mL).
yield: 2.77 g (crude product)

2-(2-(Boc(methyl)amino)pyridin-4-yl)-1-(4-fluorophenyl)ethan-1,2-dion-2-oxime

Example 5e

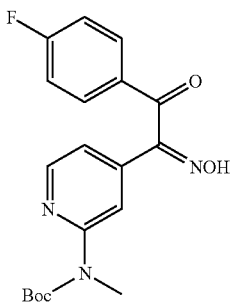

Compound 5e was prepared according to general procedure E from 4e (2.10 g, 6.1 mmol), NaNO$_2$ (1.40 g, 20.3 mmol in 10 mL water), and glacial acetic acid (50 mL).
yield: 2.30 g (crude product)

2-(2-(Boc(3-methylbutan-2-yl)amino)pyridin-4-yl)-1-(4-fluorophenyl)ethan-1,2-dion-2-oxime Example 5f

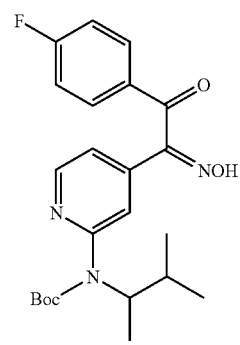

Compound 5f was prepared according to general procedure E from 4f (1.04 g, 2.6 mmol), NaNO$_2$ (0.54 g, 7.8 mmol in 10 mL water), and glacial acetic acid (30 mL).
yield: 0.93 g (crude product)

2-(2-(Boc(sec-butyl)amino)pyridin-4-yl)-1-(4-fluorophenyl)ethan-1,2-dion-2-oxime Example 5g

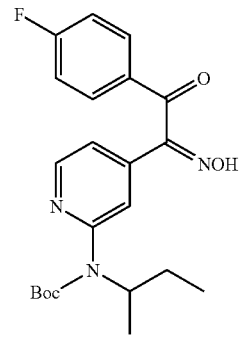

Compound 5g was prepared according to general procedure E from 4g (2.48 g, 6.4 mmol), NaNO$_2$ (1.39 g, 20.2 mmol in 2 mL water), and glacial acetic acid (50 mL).
yield: 2.20 g (crude product)

2-(2-(Boc(isopropyl)amino)pyridin-4-yl)-1-(4-fluorophenyl)ethan-1,2-dion-2-oxime Example 5h

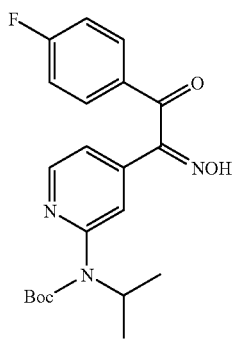

Compound 5h was prepared according to general procedure E from 4h (2.14 g, 5.8 mmol), NaNO$_2$ (1.19 g, 17.3 mmol in 20 mL water), and glacial acetic acid (50 mL).
yield: 1.68 g (crude product)

2-(2-(Boc(tetrahydro-2H-pyran-4-yl)amino)pyridin-4-yl)-1-(4-fluorphenyl)ethan-1,2-dion-2-oxime Example 5i

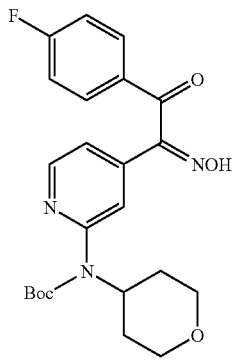

Compound 5i was prepared according to general procedure E from 4i (3.60 g, 8.7 mmol), NaNO$_2$ (1.80 g, 26.1 mmol in 5 mL water), and glacial acetic acid (75 mL).
yield: 3.20 g (crude product)

General Procedure for the Preparation of 2-Amino-2-(2-(1-Alkyl/Phenylalkylamino)Pyridin-4-Yl)-1-(4-Fluorophenyl)Ethanone Hydrochlorides (General Procedure F)

In a three-necked flask 2-(2-(boc(alkyl/phenylalkyl)amino)pyridin-4-yl)-1-(4-fluorophenyl)ethan-1,2-dion-2-oxime was dissolved in methanol and saturated methanolic hydrogen chloride. Pd/C 10% was added. The reaction flask was evacuated and flooded with hydrogen (4×). The suspension was stirred under hydrogen atmosphere at atmospheric pressure for 16 h. The catalyst was filtered off and washed thoroughly with methanol. The filtrate was concentrated in vacuo. The crude product was used without further purification for the next step.

2-Amino-1-(4-fluorophenyl)-2-(2-(1-phenylethylamino)pyridin-4-yl)ethanone hydrochloride Example 6a

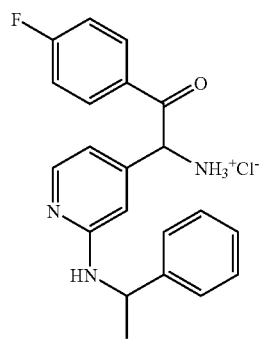

Compound 6a was prepared according to general procedure F from 5a (1.60 g), Pd/C 10% (0.45 g), methanol (20 mL) and saturated methanolic hydrogen chloride. (25 mL).
yield: 1.70 g (crude product)

2-Amino-2-(2-(1-benzylamino)pyridin-4-yl)-1-(4-fluorophenyl)ethanone hydrochloride Example 6b

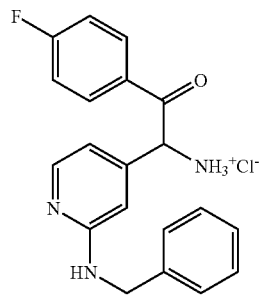

Compound 6b was prepared according to general procedure F from 5b (0.76 g), Pd/C 10% (0.25 g), methanol (15 mL) and saturated methanolic hydrogen chloride (20 mL).
yield: 0.64 g (crude product)

2-Amino-1-(4-fluorophenyl)-2-(2-(isobutylamino)pyridin-4-yl)ethanone hydrochloride Example 6c

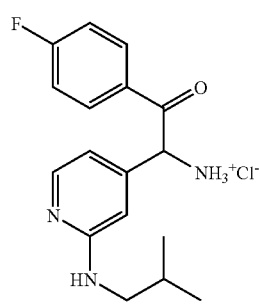

Compound 6c was prepared according to general procedure F from 5c (2.00 g), Pd/C 10% (0.30 g), methanol (20 mL) and saturated methanolic hydrogen chloride (25 mL).
yield: 2.09 g (crude product)

2-Amino-2-(2-(ethylamino)pyridin-4-yl)-1-(4-fluorophenyl)ethanone hydrochloride

Example 6d

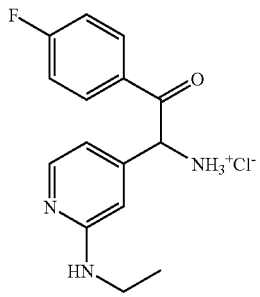

Compound 6d was prepared according to general procedure F from 5d (2.60 g), Pd/C 10% (0.35 g), methanol (15 mL) and saturated methanolic hydrogen chloride (25 mL).
yield: 2.77 g (crude product)

2-Amino-1-(4-fluorophenyl)-2-(2-(methylamino)pyridin-4-yl)ethanone-hydrochloride Example 6e

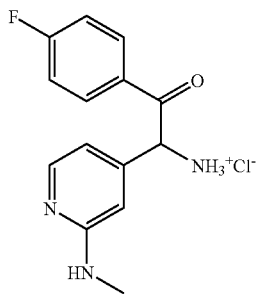

Compound 6e was prepared according to general procedure F from 5e (2.30 g), Pd/C 10% (0.30 g), methanol (20 mL) and saturated methanolic hydrogen chloride (25 mL).
yield: 1.75 g (crude product)

2-Amino-1-(4-fluorophenyl)-2-(2-(3-methylbutan-2-ylamino)pyridin-4-yl)ethanone hydrochloride Example 6f

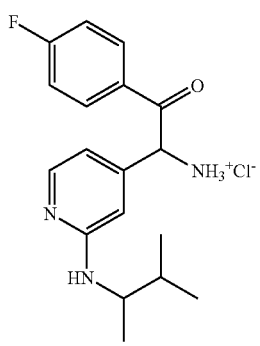

Compound 6f was prepared according to general procedure F from 5f (0.8 g), Pd/C 10% (0.25 g), methanol (15 mL) and saturated methanolic hydrogen chloride (20 mL).
yield: 0.78 g (crude product)

2-Amino-1-(4-fluorophenyl)-2-(2-(sec-butylamino)pyridin-4-yl)ethanone hydrochloride Example 6g

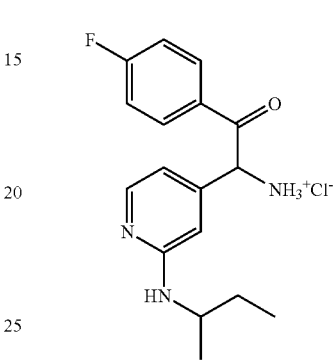

Compound 6g was prepared according to general procedure F from 5g (2.10 g), Pd/C 10% (0.50 g), methanol (25 mL) and saturated methanolic hydrogen chloride (35 mL).
yield: 2.20 g (crude product)

2-Amino-1-(4-fluorophenyl)-2-(2-(isopropylamino)pyridin-4-yl)ethanone hydrochloride Example 6h

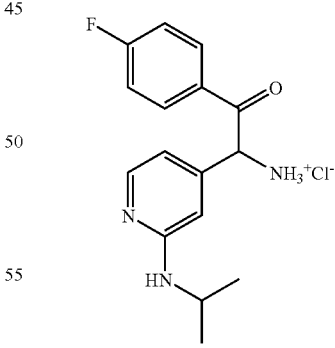

Compound 6h was prepared according to general procedure F from 5h (1.68 g), Pd/C 10% (0.45 g), methanol (15 mL) and saturated methanolic hydrogen chloride (25 mL).
yield: 1.90 g (crude product)

2-Amino-1-(4-fluorophenyl)-2-(2-(tetrahydro-2H-pyran-4-ylamino)pyridin-4-yl)ethanone hydrochloride Example 6i

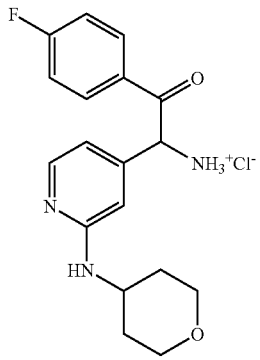

Compound 6i was prepared according to general procedure F from 5i (1.30 g), Pd/C 10% (0.50 g), methanol (20 mL) and saturated methanolic hydrogen chloride (30 mL).
yield: 1.43 g (crude product)

General Procedure for the Preparation of 5-(2-(1-Alkyl/Phenylalkylamino)Pyridin-4-Yl)-4-(4-Fluorophenyl)-1,3-Dihydroimidazol-2-Thiones (General Procedure G)

2-Amino-2-(2-(1-phenylalkylamino)pyridin-4-yl)-1-(4-fluorophenyl)ethanone hydrochloride (1.0 equiv.) was dissolved in absolute DMF and potassium thiocyanate (1.3 equiv.) was added. The reaction mixture was heated to reflux for 3 h. The suspension was cooled to room temperature and slowly diluted with water. The yellow precipitate was filtered off and washed with water.

4-(4-Fluorophenyl)-5-(2-(1-phenylethylamino)pyridin-4-yl)-1,3-dihydroimidazol-2-thione Example 7a

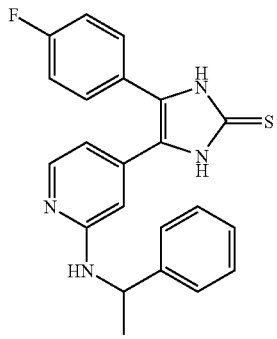

Compound 7a was prepared according to general procedure G from 6a (1.70 g), KSCN (0.60 g, 6.2 mmol), DMF (25 mL) and water (50 mL).
yield: 1.01 g (75% over 2 steps) as a yellow solid
$^1$H-NMR (DMSO) δ 1.36 (d, J=6.88 Hz, 3H, CH$_3$), 4.82-4.89 (m, 1H, CH), 6.33-6.36 (m, 2H, C$^3$—H/C$^5$—H-Pyr), 7.02 (d, J=7.74 Hz, NH, exchangeable), 7.12-7.27 (m, 7H, 5× Ph, C$^3$—/C—H 4-F-Ph), 7.36-7.43 (m, 2H, C$^2$—/C$^6$ 4-F-Ph), 7.83 (d, J=5.32 Hz, 1H, C$^6$—H-Pyr), 12.50 (d, J=7.26 Hz, 2H, 2×NH, exchangeable)
IR (ATR) ṽ (cm$^{-1}$) 3061 (Ar), 2044, 1607, 1552, 1514 (C(S)NH), 1449 (CH$_3$), 1279, 1224 (C—F), 1159, 1097, 985, 838 (Ar), 814, 700 (Ar)

5-(2-(1-Benzylamino)pyridin-4-yl)-4-(4-fluorophenyl)-1,3-dihydroimidazol-2-thione Example 7b

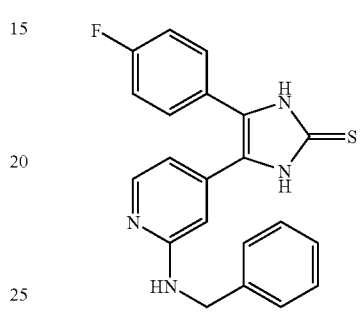

Compound 7b was prepared according to general procedure G from 6b (0.64 g), KSCN (0.22 g, 2.3 mmol), DMF (20 mL) and water (50 mL).
yield: 0.38 g (67% over 2 steps) as a yellow solid
$^1$H-NMR (DMSO) δ 4.38 (d, J=5.98 Hz, 2H, CH$_2$), 6.37-6.43 (m, 2H, C$^3$—/C$^5$—H-Pyr), 7.07-7.32 (m, 8H, NH+C$^2$—/C$^6$—H-4-F-Ph+5× Ph), 7.37-7.44 (m, 2H, C$^2$—/C$^6$—H-4-F-Ph), 7.87 (d, J=5.32 Hz, 1H, C$^6$—H-Pyr), 12.57 (bs, 2H, 2×NH)
IR (ATR) ṽ (cm$^{-1}$) 3229, 3063 (Ar), 1649, 1607, 1559, 1515 (C(S)NH), 1495, 1449, 1278, 1259, 1226 (C—F), 1160, 1092, 983, 839 (Ar), 815, 736 (Ar), 696 (Ar)

4-(4-Fluorophenyl)-5-(2-(isobutylamino)pyridin-4-yl)-1,3-dihydroimidazol-2-thione Example 7c

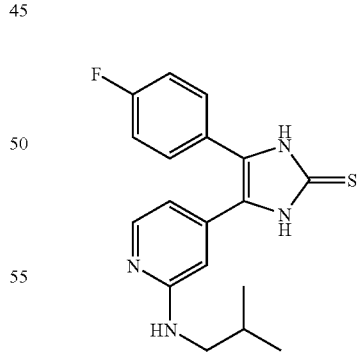

Compound 7c was prepared according to general procedure G from 6c (2.09 g), KSCN (0.61 g, 6.2 mmol), DMF (45 mL) and water (150 mL).
yield: 1.35 g (61% over 3 steps) as a yellow solid
$^1$H-NMR (DMSO) δ 0.84 (d, J=6.60 Hz, 3H, CH$_3$), 1.67-1.81 (m, 1H, CH), 2.90-2.97 (m, 2H, CH$_2$), 6.36 (d, J=5.34 Hz, 1H, C$^5$—H-Pyr), 6.43 (s, 1H, C$^3$—H-Pyr), 6.82 (bs, 1H, NH, exchangeable), 7.21-7.29 (m, 2H, C$^3$/C$^5$—H-4-F-Ph), 7.41-7.48 (m, 2H, C²/C⁶—H-4-F-Ph), 7.84 (d, J=5.38 Hz, 1H, C⁶—H-Pyr), 12.61 (bs, 2H, 2×NH, exchangeable)

IR (ATR) ṽ (cm⁻¹) 2868, 2045, 1649, 1599, 1556, 1520 (C(S)NH), 1482, 1436, 1389, 1261, 1222 (C—F), 1159, 1101, 984, 840 (Ar), 808, 666

5-(2-(Ethylamino)pyridin-4-yl)-4-(4-fluorophenyl)-1,3-dihydroimidazol-2-thione

Example 7d

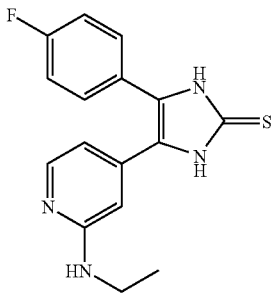

Compound 7d was prepared according to general procedure G from 6d (2.30 g), KSCN (0.85 g, 9.0 mmol), DMF (50 mL) and water (200 mL).

yield: 1.11 g (48% over 3 steps) as a yellow solid

¹H-NMR (DMSO) δ 1.07 (t, J=7.13 Hz, 3H, CH₃), 3.03-3.29 (m, 2H, CH₂), 6.33-6.39 (m, 2H, C⁵—/C³—H-Pyr) 6.53-6.57 (m, 1H, NH), 7.20-7.31 (m, 2H, C³—/C—H-4-F-Ph), 7.39-7.47 (m, 2H, C²—/C⁶—H-4-F-Ph), 7.87 (d, J=5.36 Hz, 1H, C⁶—H-Pyr), 12.59 (bs, 2H, 2×NH)

IR (ATR) Ṽ (cm⁻¹) 3240, 2971 (—CH₃), 2902, 1649, 1605, 1556, 1515 (C(S)NH), 1442 (—CH₃), 1378 (—CH₃), 1355, 1275, 1223 (C—F), 1159, 1097, 981, 840 (Ar), 813

4-(4-Fluorophenyl)-5-(2-(methylamino)pyridin-4-yl)-1,3-dihydroimidazol-2-thione

Example 7e

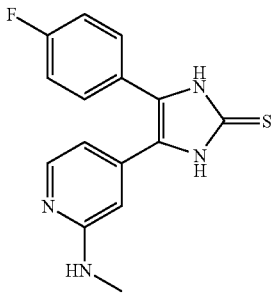

Compound 7e was prepared according to general procedure G from 6e (1.75 g), KSCN (0.75 g, 7.7 mmol), DMF (40 mL) and water (200 mL). No product precipitated. So the mother liquor was extracted with EtOAc (3×150 mL), the organic phase was dried over Na₂SO₄ and purified by flash chromatography (SiO₂, EtOAc 100%).

yield: 0.55 g (30% over 3 steps) as a yellow solid.

¹H-NMR (DMSO) δ 2.69 (t, J=4.74 Hz, 3H, CH₃), 6.33-6.39 (m, 2H, C⁵—/C³—H-Pyr), 6.45-6.52 (m, 1H, NH, exchangeable), 7.20-7.29 (m, 2H, C³—/C⁵—H-4—F-Ph), 7.40-7.48 (m, 2H, C²—/C⁶—H-4-F-Ph), 7.88 (d, J=5.30 Hz, 1H, C⁶—H-Pyr), 12.59 (bs, 2H, 2×NH, exchangeable)

IR (ATR) ṽ (cm⁻¹) 3237, 3056, 2909, 1649, 1607, 1558, 1516 (C(S)NH), 1416, 1378, 1280, 1226 (C—F), 1216, 1160, 1097, 983, 840 (Ar), 813

4-(4-Fluorophenyl)-5-(2-(3-methylbutan-2-ylamino)pyridin-4-yl)-1,3-dihydroimidazol-2-thione Example 7f

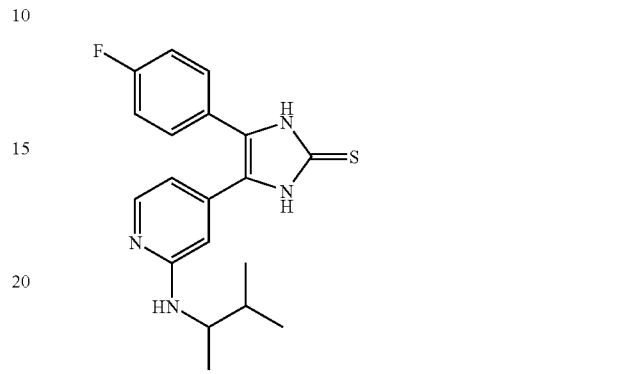

Compound 7f was prepared according to general procedure G from 6f (0.78 g), KSCN (0.39 g, 4.0 mmol), DMF (15 mL) and water (30 mL).

yield: 0.31 g (47% over 2 steps) as a yellow solid

¹H-NMR (DMSO) δ 0.82 and 0.84 (2 d, J=6.51 Hz, J₂=6.50 Hz, 6H, 2×CH₃), 0.98 (d, J=6.56 Hz, 3H, CH₃), 1.62-1.75 (m, 1H, CH), 3.55-3.65 (m, 1H, CH), 6.32 (d, J=5.18 Hz, 1H, C⁵—H-Pyr), 6.39-6.44 (m, 2H, C³—H-Pyr+NH, exchangeable), 7.20-7.28 (m, 2H, C³—/C⁵—H-4-F-Ph), 7.39-7.46 (m, 2H, C²—/C⁶—H-4-F-Ph), 7.84 (d, J=5.40 Hz, 1H, C⁶—H-Pyr), 12.53-12.60 (m, 2H, 2×NH, exchangeable)

IR (ATR) v (cm⁻¹) 2962 (—CH₃), 2048, 1607, 1551, 1512 (C(S)NH), 1388 (—CH₃), 1281, 1222 (C—F), 1158, 1102, 985, 839 (Ar)

4-(4-Fluorophenyl)-5-(2-(sec-butylamino)pyridin-4-yl)-1,3-dihydroimidazol-2-thione Example 7g

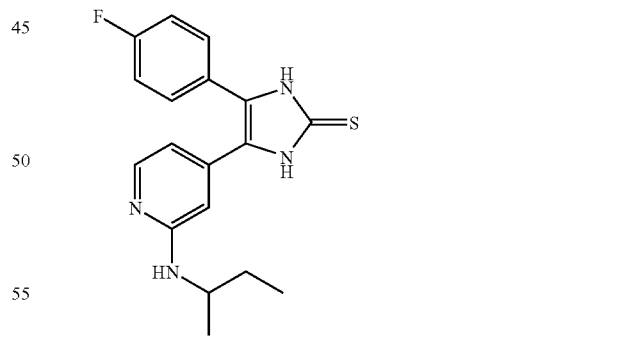

Compound 7g was prepared according to general procedure G from 6g (2.20 g), KSCN (0.67 g, 6.9 mmol), DMF (25 mL) and water (50 mL).

yield: 0.90 g (50% over 2 steps) as a yellow solid

¹H-NMR (DMSO) δ 0.78-0.86 (m, 3H, CH₃), 0.97-1.05 (m, 3H, CH₃), 1.33-1.48 (m, 2H, CH₂), 3.60-3.69 (m, 1H, CH), 6.24-6.36 (m, 3H, C³—/C⁵—H-Pyr+NH), 7.20-7.29 (m, 2H, C³—/C—H-4-F-Ph), 7.39-7.46 (m, 2H, C²—/C⁶—H-4-F-Ph), 7.85 (d, J=5.32 Hz, 1H, C⁶—H-Pyr), 12.56-12.69 (m, 2H, 2×NH)

IR (ATR) v (cm$^{-1}$) 3244, 2965 (—CH$_3$), 2926, 2037, 1648, 1607, 1552, 1512 (C(S)NH), 1454, 1383 (—CH$_3$), 1281, 1223 (C—F), 1158, 1097, 985, 839 (Ar), 813

4-(4-Fluorophenyl)-5-(2-(isopropylamino)pyridin-4-yl)-1,3-dihydroimidazol-2-thione Example 7h

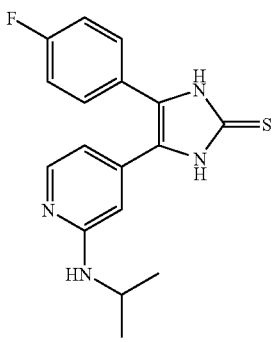

Compound 7h was prepared according to general procedure G from 6h (1.9 g), KSCN (0.52 g, 5.4 mmol), DMF (60 mL) and water (450 mL).
yield: 1.04 g (55% over 3 steps) as a yellow solid
$^1$H-NMR (DMSO) δ 1.09 (d, J=6.40 Hz, 6H, 2×CH$_3$), 3.75-3.92 (m, 1H, CH), 6.31-6.37 (m, 3H, C$^5$—H-Pyr+C$^3$—H-Pyr+NH, exchangeable), 7.20-7.29 (m, 2H, C$^3$—/C—H-4-F-Ph), 7.39-7.47 (m, 2H, C$^2$—/C$^6$—H-4-F-Ph), 7.87 (d, J=5.24 Hz, 1H, C$^6$—H-Pyr), 12.57-12.59 (m, 2H, 2×NH, exchangeable)
IR (ATR) ṽ (cm$^{-1}$) 3393, 3050, 2970 (—CH$_3$), 2899, 1610, 1545, 1506 (C(S)NH), 1466, 1441(—CH$_3$), 1385 (—CH$_3$), 1299, 1269, 1224 (C—F), 1178, 1162, 989, 840 (Ar), 813

4-(4-Fluorophenyl)-5-(2-(tetrahydro-2H-pyran-4-ylamino)pyridin-4-yl)-1,3-dihydroimidazol-2-thione Example 7i

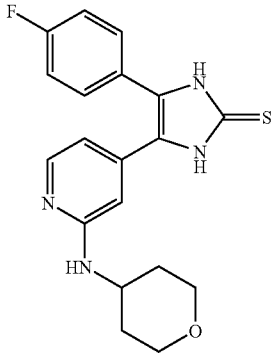

Compound 7i was prepared according to general procedure G from 6i (1.43 g), KSCN (0.45 g, 4.6 mmol), DMF (50 mL) and water (200 mL).
yield: 0.62 g (81% over 3 steps) as a yellow solid
$^1$H-NMR (DMSO) δ 1.27-1.46 (m, 2H, CH$_2$), 1.74-1.80 (m, 2H, CH$_2$), 3.27-3.37 (m, 2H, CH$_2$), 3.67-3.85 (m, 3H, CH+CH$_2$), 6.35-6.37 (m, 2H, C$^3$/C$^5$—H-Pyr), 6.49 (d, J=7.56 Hz, 1H, NH, exchangeable), 7.18-7.30 (m, 2H, C$^3$/C$^5$—H-4-F-Ph), 7.39-7.46 (m, 2H, C$^2$/C$^6$—H-4-F-Ph), 7.87 (d, J=5.88 Hz, 1H, C$^6$—H-Pyr), 12.56-12.58 (m, 2H, 2×NH, exchangeable)
IR (ATR) ṽ (cm$^{-1}$) 3253, 2972, 2897, 2848 (—CH$_2$), 1642, 1599, 1561, 1517 (C(S)NH), 1438, 1380, 1368, 1283, 1251, 1250, 1224 (C—F), 1161, 1130, 1101, 1011, 986, 842 (Ar), 832, 814, 664

General Procedure for the Synthesis of the Title Compounds (General Procedure H)

To a solution of 5-(2-(alkyl/phenylalkylamino)pyridin-4-yl)-4-(4-fluorophenyl)-1,3-dihydroimidazol-2 thiones (1.0 equiv.) and KOt-Bu (1.1 or 1.2 equiv.) in dry MeOH was added under argon atmosphere the appropriate alkylhalide (1.1 or 1.2 equiv.). The solution was heated to reflux until complete disappearance of the starting material (thiones) and cooled to room temperature. After extraction with water and EtOAc the organic phase was washed with water (2×), dried (Na$_2$SO$_4$) and evaporated under reduced pressure. The crude product was purified by flash chromatography or by crystallization.

3-(4-(4-Fluorophenyl)-5-(2-(1-phenylethylamino)pyridin-4-yl)-1H-imidazol-2-ylthio)propane-1,2-diol Example 8a

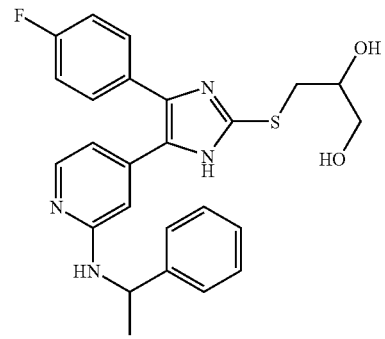

To a solution of 7a (130 mg, 0.33 mmol) and NaOEt (27 mg, 0.40 mmol) in dry MeOH (15 mL) was added under argon atmosphere 3-bromo-1,2-propanediol (62 mg, 0.40 mol). The solution was stirred 5 h at room temperature and 3 h at 50° C. Then cooled to room temperature and the crude product was purified by flash chromatography (SiO$_2$, from DCM/EtOH 9:1 to DCM/EtOH 1:1) to yield 73 mg (48%) of compound 8a.
$^1$H-NMR (MeOD) δ 1.45 (d, J=6.85 Hz, 3H, CH$_3$), 3.12-3.33 (m, CH$_2$+solvent peak), 3.63 (d, J=5.53 Hz, 2H, CH$_2$), 3.82-3.94 (m, 1H, CH), 4.65-4.76 (m, 1H, CH), 6.48 (s, 1H, C$^3$—H-Pyr), 6.57 (dd, J$_1$=5.47 Hz, J$_2$=1.52 Hz, 1H, C$^5$—H-Pyr), 7.06-7.26 (m, 7H, C$^3$/C$^5$—H-4-F-Ph+5 Ph), 7.36-7.44 (m, 2H, C$^2$/C$^6$—H-4-F-Ph), 7.80 (d, J$_1$=5.50 Hz, J$_2$=0.62 Hz 1H, C$^6$—H-Pyr)
IR (ATR) ṽ (cm$^{-1}$) 3058, 2927, 2865, 1646, 1609, 1549, 1503, 1449, 1355, 1223 (C—F), 1158, 1094, 1069, 1032, 991, 838 (Ar), 813, 761, 700 (Ar)

3-(5-(2-(1-Benzylamino)pyridin-4-yl)-4-(4-fluorophenyl)-1H-imidazol-2-ylthio)propane-1,2-diol Example 8b

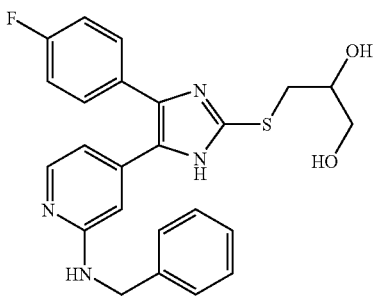

Compound 8b was prepared according to general procedure H from 7b (150 mg, 0.40 mmol), KOt-Bu (54 mg, 0.48 mmol), 3-bromo-1,2-propanediol (74 mg, 0.44 mol) and MeOH (8 mL).
reaction time: 4.5 h
flash chromatography: $SiO_2$, from DCM/EtOH 95:5 to DCM/EtOH 75:25
yield: 49 mg (27%)
$^1$H-NMR (MeOD) δ 3.12-3.36 (m, $CH_2$+solvent peak), 3.63 (d, J=5.43 Hz, 2H, $CH_2$), 3.83-3.94 (m, 1H, CH), 4.39 (s, 2H, $CH_2$), 6.58-6.61 (m, 2H, $C^3/C^5$—H-Pyr), 7.05-7.14 (m, 2H, $C^3/C^5$—H-4-F-Ph), 7.17-7.27 (m, 5H, 5× Ph), 7.37-7.46 (m, 2H, $C^2/C^6$—H-4-F-Ph), 7.83 (d, J=5.91 Hz, $C^6$—H-Pyr)
IR (ATR) ṽ ($cm^{-1}$) 2918, 1609, 1548, 1503, 1356, 1221 (C—F), 1157, 1069, 1032, 838 (Ar), 733 (Ar), 696 (Ar)

3-(4-(4-Fluorophenyl)-5-(2-(isobutylamino)pyridin-4-yl)-1H-imidazol-2-ylthio)propane-1,2-diol Example 8c

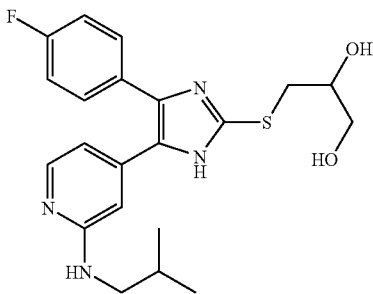

Compound 8c was prepared according to general procedure H from 7c (150 mg, 0.44 mmol), KOt-Bu (59 mg, 0.53 mmol), 3-bromo-1,2-propanediol (82 mg, 0.53 mol) and MeOH (8 mL).
reaction time: 2.5 h
flash chromatography: $SiO_2$, from DCM/EtOH 95:5 to DCM/EtOH 75:25
yield: 53 mg (29%)
$^1$H-NMR (MeOD) δ 0.92 (d, J=6.64 Hz, 6H, 2×$CH_3$), 1.18 (t, J=6.73 Hz, H, CH), 2.97 (d, J=6.99 Hz, 2H, $CH_2$), 3.13-3.38 (m, $CH_2$+solvent peak), 3.64 (d, J=5.40 Hz, 2H, $CH_2$), 3.84-3.95 (m, 1H, CH), 6.54-6.57 (m, 2H, $C^3/C^5$—H-Pyr), 7.10-7.19 (m, 2H, $C^3/C^5$—H-4-F-Ph), 7.42-7.52 (m, 2H, $C^2/C^6$—H-4-F-Ph), 7.80 (d, J=6.08 Hz, 1H, $C^6$—H-Pyr)
IR (ATR) ṽ ($cm^{-1}$) 2870, 1609, 1548, 1502, 1471, 1429, 1222 (C—F), 1158, 987, 842 (Ar), 813

3-(5-(2-(Ethylamino)pyridin-4-yl)-4-(4-fluorophenyl)-1H-imidazol-2-ylthio)propane-1,2-diol Example 8d

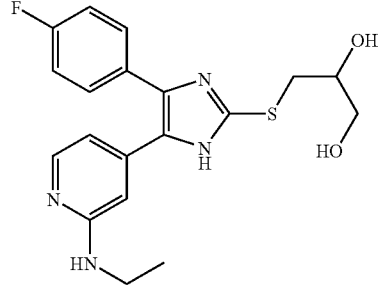

Compound 8d was prepared according to general procedure H from 7d (200 mg, 0.64 mmol), KOt-Bu (86 mg, 0.76 mmol), 3-bromo-1,2-propanediol (118 mg, 0.76 mol) and MeOH (10 mL).
reaction time: 3 h
flash chromatography: $SiO_2$, from DCM/EtOH 95:5 to DCM/EtOH 75:25
yield: 41 mg (17%)
$^1$H-NMR (MeOD) δ 1.18 (t, J=7.18 Hz, 3H, $CH_3$), 3.13-3.38 (m, 2×$CH_2$+solvent peak), 3.62-3.65 (m, $CH_2$), 3.83-3.94 (m, 1H, CH), 6.54-6.57 (m, 2H, $C^3/C^5$—H-Pyr), 7.11-7.20 (m, 2H, $C^3/C^5$—H-4-F-Ph), 7.44-7.51 (m, 2H, $C^2/C^6$—H-4-F-Ph), 7.81 (d, J=5.22 Hz, 1H, $C^6$—H-Pyr)
IR (ATR) v ($cm^{-1}$) 2865, 1608, 1533, 1501, 1408, 1377, 1223 (C—F), 1071, 988, 841 (Ar), 811

3-(4-(4-Fluorophenyl)-5-(2-(methylamino)pyridin-4-yl)-1H-imidazol-2-ylthio)propane-1,2-diol Example 8e

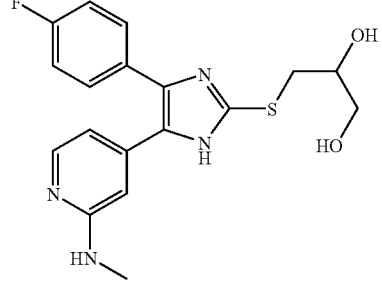

Compound 8e was prepared according to general procedure H from 7e (150 mg, 0.5 mmol), KOt-Bu (67 mg, 0.6 mmol), 3-bromo-1,2-propanediol (92 mg, 0.6 mmol) and MeOH (8 mL).
reaction time: 3 h
flash chromatography: $SiO_2$, from DCM/EtOH 95:5 to DCM/EtOH 75:25
yield: 47 mg (25%)

$^1$H-NMR (MeOD) δ 2.80 (s, 3H, CH$_3$), 3.14-3.38 (m, CH$_2$+solvent peak), 3.64 (d, J=5.40 Hz, CH$_2$), 3.84-3.95 (m, 1H, CH), 6.54-6.56 (m, 2H, C$^3$/C$^5$—H-4-F-Ph), 7.09-7.18 (m, 2H, C$^3$/C$^5$—H-4-F-Ph), 7.42-7.49 (m, 2H, C$^2$/C$^6$—H-4-F-Ph), 7.82 (d, J=5.40 Hz, 1H, C$^6$—H-Pyr)

IR (ATR) ṽ (cm$^{-1}$) 2926, 1609, 1550, 1504, 1412, 1290, 1222 (C—F), 1158, 1075, 1034, 988, 838 (Ar), 813

3-(4-(4-Fluorophenyl)-5-(2-(3-methylbutan-2-ylamino)pyridin-4-yl)-1H-imidazol-2-ylthio)propane-1,2-diol Example 8f

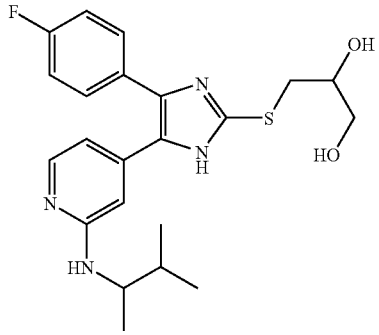

Compound 8f was prepared according to general procedure H from 7f (100 mg, 0.28 mmol), KOt-Bu (35 mg, 0.31 mmol), 3-bromo-1,2-propanediol (48 mg, 0.31 mol) and MeOH (6.5 mL).
reaction time: 3 h
flash chromatography: SiO$_2$, from DCM/MeOH 95:5 to DCM/MeOH 80:20
yield: 50 mg (41%)

$^1$H-NMR (MeOD) δ 0.83-0.93 (m, 6H, 2×CH$_3$), 1.05-1.08 (m, 3H, CH$_3$), 1.68-1.78 (m, 1H, CH), 3.13-3.37 (m, CH$_2$+solvent peak), 3.49-3.55 (m, 1H, CH), 3.64 (d, J=5.40 Hz, CH$_2$), 3.86-3.91 (m, 1H, CH), 6.50-6.52 (m, 2H, C$^3$/C$^5$—H-Pyr), 7.10-7.19 (m, 2H, C$^3$/C$^5$—H-4-F-Ph), 7.37-7.50 (m, 2H, C$^2$/C$^6$—H-4-F-Ph), 7.80 (d, J=4.81 Hz, 1H, C$^6$—H-Pyr)

IR (ATR) ṽ (cm$^{-1}$) 2924, 2854, 1608, 1548, 1504, 1457, 1223 (C—F), 1158, 1096, 1036, 987, 839 (Ar), 813

3-(4-(4-Fluorophenyl)-5-(2-(sec-butylamino)pyridin-4-yl)-1H-imidazol-2-ylthio)propane-1,2-diol Example 8g

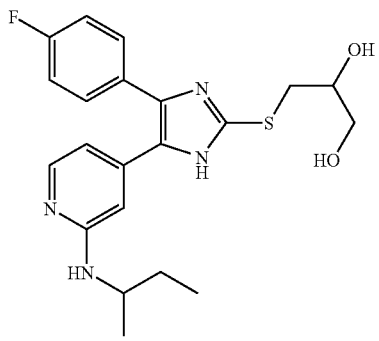

Compound 8g was prepared according to general procedure H from 7g (100 mg, 0.29 mmol), KOt-Bu (50 mg, 0.32 mmol), 3-bromo-1,2-propanediol (33 mg, 0.29 mol) and MeOH (8 mL).
reaction time: 3 h
flash chromatography: SiO$_2$, from DCM/EtOH 95:5 to DCM/EtOH 80:20
yield: 31 mg (26%)

$^1$H-NMR (MeOD) δ 0.87-0.95 (m, 3H, CH$_3$), 1.14 (d, J=6.42 Hz, 3H, CH$_3$), 1.43-1.56 (m, 2H, CH$_2$), 3.17-3.38 (m, CH$_2$+solvent peak), 3.55-3.65 (m, 3H, CH+CH$_2$), 3.84-3.93 (m, H, CH), 6.54-6.59 (m, 2H, C$^3$/C$^5$—H-Pyr), 7.11-7.20 (m, 2H, C$^3$/C$^5$—H-4-F-Ph), 7.44-7.52 (m, 2H, C$^2$—/C$^6$—H-4-F-Ph), 7.78 (d, J=5.46 Hz, 1H, C$^6$—H-Pyr)

IR (ATR) ṽ (cm$^{-1}$) 2924, 1608, 1548, 1503, 1457, 1376 (—CH$_3$), 1222 (C—F), 1158, 1095, 1035, 987, 838 (Ar), 814

3-(4-(4-Fluorophenyl)-5-(2-(isopropylamino)pyridin-4-yl)-1H-imidazol-2-ylthio)propane-1,2-diol Example 8h

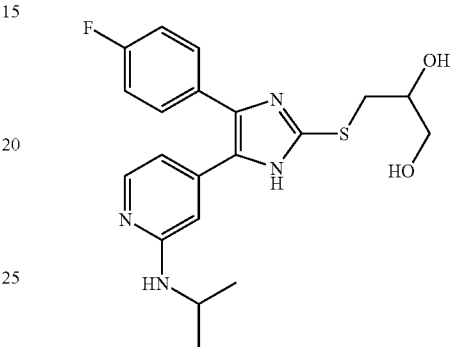

Compound 8h was prepared according to general procedure H from 7h (100 mg, 0.30 mmol), KOt-Bu (34 mg, 0.33 mmol), 3-bromo-1,2-propanediol (52 mg, 0.33 mol) and MeOH (8 mL).
reaction time: 3.5 h at 55° C.
flash chromatography: SiO$_2$, from DCM/EtOH 95:5 to DCM/EtOH75:25
yield: 70 mg (59%)

$^1$H-NMR (MeOD) δ 1.15 (d, J=6.30 Hz, 6H, 2×CH$_3$), 3.13-3.37 (m, CH$_2$+solvent peak), 3.62-3.65 (m, 2H, CH$_2$), 3.75-3.91 (m, 2H, 2×CH), 6.51-6.53 (m, 2H, C$^3$/C$^5$—H-Pyr), 7.10-7.19 (m, 2H, C$^3$/C$^5$—H-4-F-Ph), 7.43-7.50 (m, 2H, C$^2$—/C$^6$—H-4-F-Ph), 7.80-7.82 (m, 1H, C$^6$—H-Pyr)

IR (ATR) ṽ (cm$^{-1}$) 3340, 2974 (—CH$_3$), 2932, 1607, 1577, 1530, 1500, 1455, 1417, 1385 (—CH$_3$), 1221 (C—F), 1129, 1091, 1073, 999, 988, 904, 840 (Ar), 813, 735, 722, 680

3-(4-(4-Fluorophenyl)-5-(2-(tetrahydro-2H-pyran-4-ylamino)pyridin-4-yl)-1H-imidazol-2-ylthio)propane-1,2-diol Example 8i

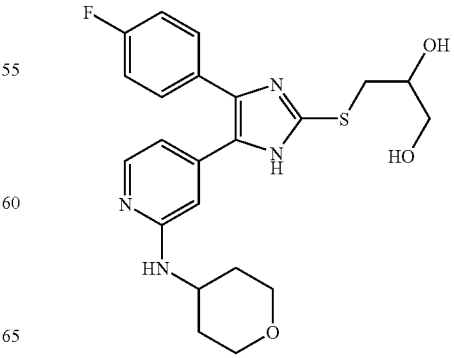

Compound 8i was prepared according to general procedure H from 7i (150 mg, 0.41 mmol), KOt-Bu (54 mg, 0.48 mmol), 3-bromo-1,2-propanediol (75 mg, 0.48 mol) and MeOH (8 mL).

reaction time: 3.5 h flash chromatography: SiO$_2$, from DCM/EtOH 95:5 to DCM/EtOH 75:25 yield: 58 mg (31%)

$^1$H-NMR (DMSO) δ 1.24-1.46 (m, 2H, CH$_2$), 1.77-1.83 (m, 2H, CH$_2$), 3.08-3.39 (m, CH$_2$+CH+solvent peak), 3.74-3.86 (m, 4H, 2×CH$_2$), 4.86 (s, 1H, OH, exchangeable), 5.30 (s, 1H, OH, exchangeable), 6.42-6.63 (m, 3H, C$^3$/C$^5$—H-Pyr+NH, exchangeable), 7.18-7.32 (m, 2H, C$^3$—H/C$^5$—H-4-F-Ph), 7.44-7.50 (m, 2H, C$^2$—H/C$^6$—H-4-F-Ph), 7.81-7.91 (m, 1H, C$^6$—H-Pyr), 12.68 (bs, 1H, NH, exchangeable)

IR (ATR) ṽ (cm$^{-1}$) 2849, 1608, 1549, 1503, 1366, 1221 (C—F), 1157, 1136, 1083, 1011, 983, 839 (Ar), 813

3-(4-(4-Fluorophenyl)-5-(2-(3-methylbutan-2-ylamino)pyridin-4-yl)-1H-imidazol-2-ylthio)propane-1-ol Example 8j

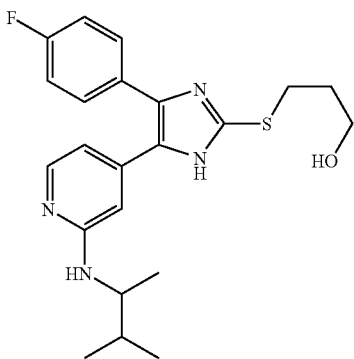

Compound 8j was prepared according to general procedure H from 7f (300 mg, 0.84 mmol), KOt-Bu (104 mg, 0.93 mmol), 3-bromo-1-propanol (129 mg, 0.93 mol) and MeOH (20 mL).

reaction time: 1 h flash chromatography: SiO$_2$, from DCM/MeOH 95:5 to DCM/MeOH 85:15 yield: 140 mg (40%)

$^1$H-NMR (MeOD) δ 0.88 and 0.90 (2d, J=6.8 Hz and J=6.8 Hz, 6H, 2×CH$_3$), 1.06 (d, J=6.60 Hz, 3H, CH$_3$), 1.67-1.81 (m, 1H, CH), 1.85-1.95 (m, 2H, CH$_2$), 3.17 (t, J=7.05 Hz, 2H, CH$_2$), 3.50 (q, J=6.34 Hz, 1H, CH), 3.70 (t, J=6.04 Hz, CH$_2$), 6.50-6.54 (m, 2H, C$^3$/C$^5$—H-Pyr), 7.07-7.16 (m, 2H, C$^3$/C$^5$—H-4-F-Ph), 7.41-7.48 (m, 2H, C$^2$/C$^6$—H-4-F-Ph), 7.80 (dd, J=5.09 Hz, J$_2$=0.69 Hz, 1H, C$^6$—H-Pyr)

IR (ATR) ṽ (cm$^{-1}$) 2959, 2926, 2854, 1607, 1547, 1504, 1433, 1369, 1221 (C—F), 1157, 1096, 1043, 983, 838 (Ar), 813

2-(4-(4-Fluorophenyl)-5-(2-(3-methylbutan-2-ylamino)pyridin-4-yl)-1H-imidazol-2-ylthio)ethanol Example 8k

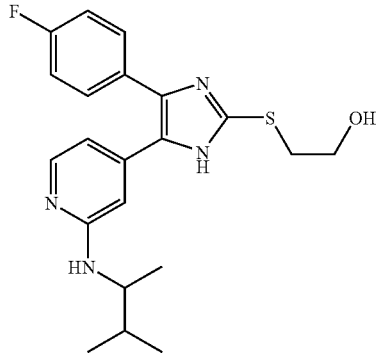

Compound 8k was prepared according to general procedure H from 7f (300 mg, 0.84 mmol), KOt-Bu (104 mg, 0.93 mmol), 2-bromoethanol (116 mg, 0.93 mol) and MeOH (20 mL).

reaction time: 1.5 h flash chromatography: SiO$_2$, from DCM/MeOH 95:5 to DCM/MeOH 85:15 yield: 80 mg (24%)

$^1$H-NMR (MeOD) δ 0.90 and 0.92 (2d, J=6.8 Hz and J=6.8 Hz, 6H, 2×CH$_3$), 1.07 (d, J=6.61 Hz, 3H, CH$_3$), 1.65-1.81 (m, 1H, CH), 3.19 (t, J=6.26 Hz, CH$_2$), 3.47-3.55 (m, 1H, CH), 3.81 (t, J=6.26 Hz, CH$_2$), 6.50-6.52 (m, 2H, C$^3$/C$^5$—H-Pyr), 7.10-7.19 (m, 2H, C$^3$/C$^5$—H-4-F-Ph), 7.42-7.50 (m, 2H, C$^2$/C$^6$—H-4-F-Ph), 7.81 (d, J=6.19 Hz, 1H, C$^6$—H-Pyr)

IR (ATR) ṽ (cm$^{-1}$) 2960, 1607, 1547, 1504, 1221 (C—F), 1157, 1068, 983, 838 (Ar), 814

(2R)-3-(4-(4-Fluorophenyl)-5-(2-(3-methylbutan-2-ylamino)pyridin-4-yl)-1H-imidazol-2-ylthio)propane-1,2-diol Example 8l

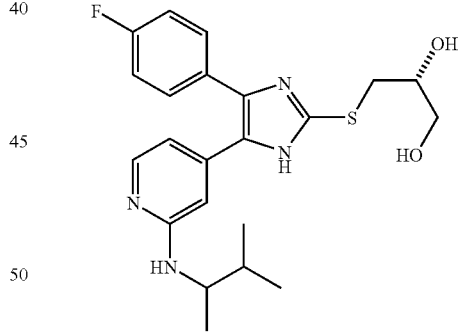

Compound 8l was prepared according to general procedure H from 7f (300 mg, 0.84 mmol), KOt-Bu (104 mg, 0.93 mmol), (R)-(−)-3-chloro-1,2-propanediol (103 mg, 0.93 mol) and MeOH (20 mL).

reaction time: 1.25 h flash chromatography: SiO$_2$, from DCM/MeOH 95:5 to DCM/MeOH 85:15 yield: 170 mg (47%)

$^1$H-NMR (MeOD) δ 0.89 and 0.91 (2d, J=6.7 Hz and J=6.8 Hz, 6H, 2×CH$_3$), 1.06 (d, J=6.59 Hz, 3H, CH$_3$), 1.64-1.81 (m, 1H, CH), 3.17-3.35 (m, CH$_2$+solvent peak), 3.46-3.65 (m, 1H, CH), 3.64 (d, J=5.38 Hz, CH$_2$), 3.84-3.95 (m, 1H, CH), 6.49-6.52 (m, 2H, C$^3$/C$^5$—H-Pyr), 7.08-7.17 (m, 2H, C$^3$/C$^5$—H-4-F-Ph), 7.42-7.49 (m, 2H, C$^2$/C$^6$—H-4-F-Ph), 7.79 (d, J=6.08 Hz, 1H, C$^6$—H-Pyr)

IR (ATR) ṽ (cm⁻¹) 3103, 2960, 2871, 1607, 1547, 1504, 1439, 1389, 1368, 1222 (C—F), 1157, 1095, 1035, 987, 838 (Ar), 813

(2S)-3-(4-(4-Fluorophenyl)-5-(2-(3-methylbutan-2-ylamino)pyridin-4-yl)-1H-imidazol-2-ylthio)propane-1,2-diol Example 8m

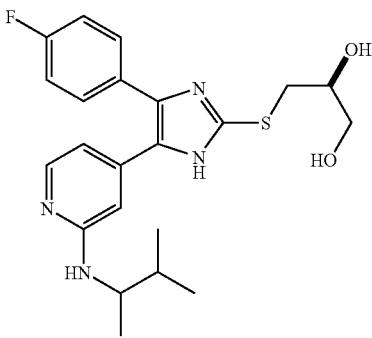

Compound 8m was prepared according to general procedure H from 7f (300 mg, 0.84 mmol), KOt-Bu (104 mg, 0.93 mmol), (S)-(+)-3-chloro-1,2-propanediol (103 mg, 0.93 mol) and MeOH (20 mL).
reaction time: 1.25 h
flash chromatography: SiO$_2$, from DCM/MeOH 95:5 to DCM/MeOH 85:15
yield: 210 mg (58%)
$^1$H-NMR (MeOD) δ 0.90 and 0.91 (2d, J=6.8 Hz and J=6.8 Hz, 6H, 2×CH$_3$), 1.07 (m, J=6.61 Hz, 3H, CH$_3$), 1.65-1.82 (m, 1H, CH), 3.14-3.35 (m, CH$_2$+solvent peak), 3.47-3.55 (m, 1H, CH), 3.64 (d, J=5.38 Hz, CH$_2$), 3.83-3.94 (m, 1H, CH), 6.50-6.53 (m, 2H, C$^3$/C$^5$—H-Pyr), 7.10-7.19 (m, 2H, C$^3$/C$^5$—H-4-F-Ph), 7.44-7.51 (m, 2H, C$^2$/C$^6$—H-4-F-Ph), 7.81 (d, J=6.35 Hz, 1H, C$^6$—H-Pyr)
IR (ATR) ṽ (cm⁻¹) 3103, 2961, 1608, 1548, 1504, 1440, 1389, 1368, 1222 (C—F), 1158, 1095, 1035, 987, 838 (Ar), 813

(2R)-3-(4-(4-Fluorophenyl)-5-(2-(isopropylamino)pyridin-4-yl)-1H-imidazol-2-ylthio)propane-1,2-diol Example 8n

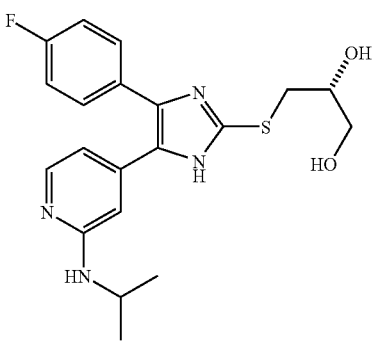

Compound 8n was prepared according to general procedure H from 7h (200 mg, 0.61 mmol), KOt-Bu (75 mg, 0.67 mmol), (R)-(−)-3-chloro-1,2-propanediol (74 mg, 0.67 mol) and MeOH (15 mL).
reaction time: 1 h
purification: crystallization from MeOH/Et$_2$O/n-hexane
yield: 113 mg (46%)
$^1$H-NMR (DMSO) δ 1.08 (d, J=6.40 Hz, 6H, 2×CH$_3$), 3.13-3.42 (m, 2×CH$_2$+H$_2$O in DMSO), 3.67-3.92 (m, 2H, 2×CH), 6.29 (d, J=7.28 Hz, 1H), 6.37 (dd, J$_1$=5.36 Hz, J$_2$=1.25 Hz, 1H, C$^5$—H-Pyr), 6.47 (s, 1H, C$^3$—H-Pyr), 7.17-7.26 (m, 2H, C$^3$/C$^5$—H-4-F-Ph), 7.43-7.50 (m, 2H, C$^2$/C$^6$—H-4-F-Ph), 7.84 (d, J=4.69 Hz, 1H, C$^6$—H-Pyr)
IR (ATR) ṽ (cm⁻¹) 3321, 2970, 2871, 1607, 1578, 1530, 1500, 1454, 1385, 1220 (C—F), 1091, 1072, 988, 866, 840 (Ar), 813

(2S)-3-(4-(4-Fluorophenyl)-5-(2-(isopropylamino)pyridin-4-yl)-1H-imidazol-2-ylthio)propane-1,2-diol Example 8o

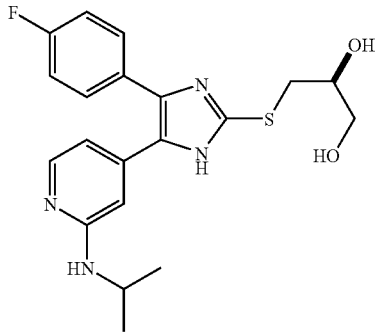

Compound 8o was prepared according to general procedure H from 7h (200 mg, 0.61 mmol), KOt-Bu (75 mg, 0.67 mmol), (S)-(+)-3-chloro-1,2-propanediol (74 mg, 0.67 mol) and MeOH (15 mL).
reaction time: 1 h
purification: crystallization from MeOH/Et$_2$O/n-hexane
yield: 119 mg (49%)
$^1$H-NMR (DMSO) δ 1.08 (d, J=6.41 Hz, 6H, 2×CH$_3$), 3.08-3.43 (m, 2×CH$_2$+H$_2$O in DMSO), 3.69-3.93 (m, 2H, 2×CH), 6.30 (d, J=7.55 Hz, 1H), 6.39 (dd, J$_1$=5.34 Hz, J$_2$=1.25 Hz, 1H, C$^5$—H-Pyr), 6.49 (s, 1H, C$^3$—H-Pyr), 7.17-7.26 (t, J=8.81 Hz, 2H, C$^3$/C$^5$—H-4-F-Ph), 7.44-7.51 (m, 2H, C$^2$/C$^6$—H-4-F-Ph), 7.85 (d, J=5.18 Hz, 1H, C$^6$—H-Pyr)
IR (ATR) ṽ (cm⁻¹) 3321, 2970, 2871, 1607, 1578, 1530, 1500, 1455, 1385, 1220 (C—F), 1091, 1073, 988, 866, 840 (Ar), 813 methyl 2-(4-(4-fluorophenyl)-5-(2-(1-phenylethylamino)pyridin-4-yl)-1H-imidazol-2-ylthio)acetate Example 8p

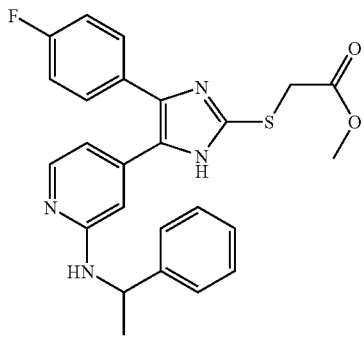

To a solution of 7a (100 mg, 0.25 mmol) and NaOEt (20 mg, 0.30 mmol) in dry MeOH (15 mL) was added under argon atmosphere the methylbromoacetate (46 mg, 0.30 mmol). The solution was stirred at 50° C. for 5 h and cooled to room temperature. After extraction with water and EtOAc the organic phase was washed with water (2×), dried (Na$_2$SO$_4$) and evaporated under reduced pressure. The crude product was purified by flash chromatography (SiO$_2$, EtOAc) to yield 40 mg (35%) of compound 8p.

$^1$H-NMR (MeOD) δ 1.45 (d, J=6.80 Hz, 3H, CH$_3$), 3.69 (s, 3H, CH$_3$), 3.86 (s, 2H, CH$_2$), 6.48 (s, 1H, C$^3$—H-Pyr), 6.58 (d, J=5.34 Hz, 1H, C$^5$—H-Pyr), 7.11-7.26 (m, 7H, 5× Ph+C$^3$/C$^5$—H-4-F-Ph), 7.36-7.43 (m, 2H, C$^2$—/C$^6$—H-4-F-Ph), 7.82 (d, J=5.40 Hz, 1H, C$^6$—H-Pyr)

IR (ATR) ṽ (cm$^{-1}$) 3416, 2592, 1762, 1601, 1546, 1505, 1447, 1430, 1292, 1215, 1153, 990, 971, 839 (Ar), 812, 760, 700 (Ar)

2-(4-(4-fluorophenyl)-5-(2-(1-phenylethylamino)pyridin-4-yl)-1H-imidazol-2-ylthio)acetic acid Example 8q

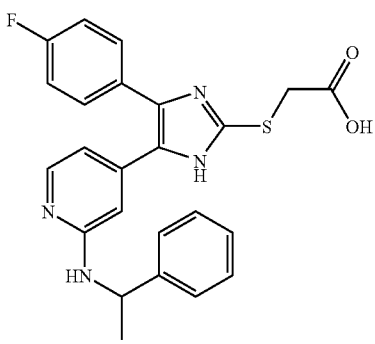

To a solution of 7a (100 mg, 0.25 mmol) and NaOEt (20 mg, 0.30 mmol) in dry MeOH (15 mL) was added under argon atmosphere 2-bromoacetic acid (41 mg, 0.30 mmol). The solution was stirred at 50° C. for 5 h and cooled to room temperature. After extraction with water and EtOAc the organic phase was washed with water (2×), dried (Na$_2$SO$_4$) and evaporated under reduced pressure. The crude product was purified by flash chromatography (SiO$_2$, from EtOAc/MeOH 85:15 to 100% MeOH) to yield 23 mg (21%) of compound 8q.

$^1$H-NMR (MeOD) δ 1.45 (d, J=6.03 Hz, 3H, CH$_3$), 3.67 (s, 2H, CH$_2$), 6.50 (s, 1H, C$^3$—H-Pyr), 6.57 (d, J=5.34 Hz, 1H, C$^5$—H-Pyr), 7.05-7.25 (m, 7H, 5× Ph+C$^3$/C$^5$—H-4-F-Ph), 7.38-7.44 (m, 2H, C$^2$—/C$^6$—H-4-F-Ph), 7.80 (d, J=5.54 Hz, 1H, C$^6$—H-Pyr)

IR (ATR) ṽ (cm$^{-1}$) 2924, 1604, 1547, 1500, 1448, 1384, 1221, 1157, 838 (Ar), 814, 700 (Ar)

Diethyl (4-(4-fluorophenyl)-5-(2-(1-phenylethylamino)pyridin-4-yl)-1H-imidazol-2-ylthio)methylphosphonate Example 8r

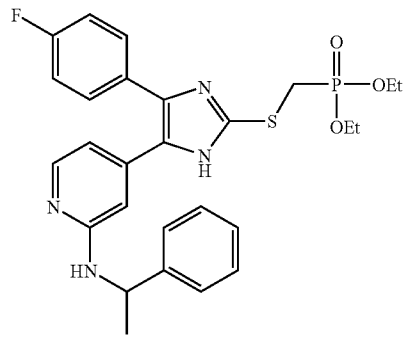

To a solution of 7a (100 mg, 0.25 mmol) and NaOEt (20 mg, 0.30 mmol) in dry MeOH (15 mL) was added under argon atmosphere the diethyl iodomethylphosphonate (83 mg, 0.30 mmol). The solution was stirred at 50° C. for 5 h and cooled to room temperature. The crude product was purified by flash chromatography (SiO$_2$, EtOAc) to yield 17 mg (13%) of compound 8r.

$^1$H-NMR (MeOD) δ 1.23 (t, J=7.07 Hz, 6H, 2×CH$_3$), 1.46 (d, J=6.84 Hz, 3H, CH$_3$), 3.50 (d, J=12.35 Hz, 2H, CH$_2$), 4.02-4.17 (m, 4H, 2×CH$_2$), 4.62-4.74 (m, 1H, CH), 6.48 (s, 1H, C$^3$—H-Pyr), 6.57-6.60 (m, 1H, C$^5$—H-Pyr), 7.08-7.25 (m, 7H, 5× Ph+C$^3$/C$^5$—H-4-F-Ph), 7.37-7.44 (m, 2H, C$^2$—/C$^6$—H-4-F-Ph), 7.83 (d, J=5.40 Hz, 1H, C$^6$—H-Pyr)

IR (ATR) ṽ (cm$^{-1}$) 3415, 2924, 2854, 1761, 1603, 1546, 1505, 1447, 1430, 1292, 1215, 1159, 1016, 971, 838 (Ar), 812, 760, 700 (Ar)

Methyl 2-(4-(4-fluorophenyl)-5-(2-(3-methylbutan-2-ylamino)pyridin-4-yl)-1H-imidazol-2-ylthio)acetate Example 8s

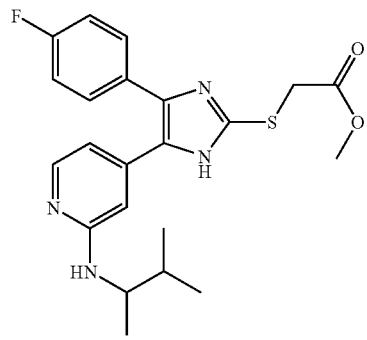

Compound 8s was prepared according to general procedure H from 7f (300 mg, 0.84 mmol), KOt-Bu (104 mg, 0.93 mmol), methyl 2-bromoacetate (142 mg, 0.93 mmol) and MeOH (20 mL).
reaction time: 1 h
flash chromatography: SiO$_2$, from petroleum ether/EtOAc 3:7 to EtOAc 100%
yield: 140 mg (42%)

$^1$H-NMR (MeOH) δ 0.85-0.94 (m, 6H, 2×CH$_3$), 1.08 (d, J=6.60 Hz, 3H, CH$_3$), 1.65-1.82 (m, 1H, CH), 3.45-3.58 (m, 1H, CH), 3.72 (s, 3H, CH$_3$), 3.89 (s, 2H, CH$_2$), 6.52-6.56 (m, 2H, C$^3$/C$^5$—H Pyr), 7.11-7.20 (m, 2H, C$^3$/C$^5$—H-4-F-Ph), 7.44-7.51 (m, 2H, C$^2$—/C$^6$—H-4-F-Ph), 7.80 (d, J=5.52 Hz, 1H, C$^6$—H-Pyr)

IR (ATR) ṽ (cm$^{-1}$) 2958, 2926, 2871, 1737, 1606, 1547, 1502, 1434, 1388, 1295, 1220 (C—F), 1156, 978, 838 (Ar), 813

Methyl 2-(4-(4-fluorophenyl)-5-(2-(isopropylamino)pyridin-4-yl)-1H-imidazol-2-ylthio)acetate Example 8t

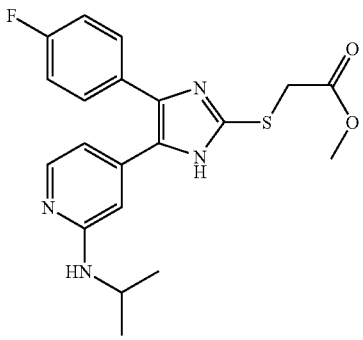

Compound 8t was prepared according to general procedure H from 7h (200 mg, 0.61 mmol), KOt-Bu (75 mg, 0.67 mmol), methyl 2-bromoacetate (102 mg, 0.67 mmol) and MeOH (15 mL).

reaction time: 1 h flash chromatography: SiO$_2$, from petroleum ether/EtOAc 3:7 to EtOAc 100% yield: 108 mg (44%)

$^1$H-NMR (MeOH) δ 1.17 (d, J=6.40 Hz, 6H, 2×CH$_3$), 3.72 (s, 3H, CH$_3$), 3.74-3.84 (m, 1H, CH), 3.89 (s, 2H, CH$_2$), 6.53-6.55 (m, 2H, C$^3$/C$^5$—H Pyr), 7.11-7.20 (m, 2H, C$^3$/C$^5$—H-4-F-Ph), 7.44-7.51 (m, 2H, C$^2$—/C$^6$—H-4-F-Ph), 7.82 (d, J=5.03 Hz, 1H, C$^6$—H-Pyr)

IR (ATR) ṽ (cm$^{-1}$) 3349, 2972, 2869, 1734, 1606, 1544, 1502, 1454, 1383, 1300, 1216 (C—F), 1152, 1126, 991 968, 880, 839, 813

2-(4-(4-Fluorophenyl)-5-(2-(isopropylamino)pyridin-4-yl)-1H-imidazol-2-ylthio)ethanol Example 8u

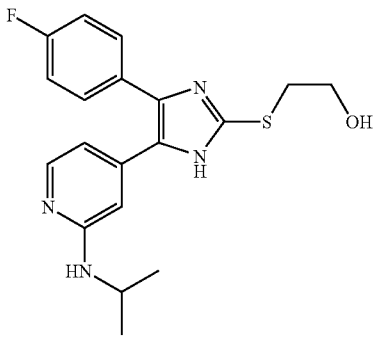

Compound 8u was prepared according to general procedure H from 7h (150 mg, 0.46 mmol), KOt-Bu (56 mg, 0.50 mmol), 2-bromoethanol (63 mg, 0.50 mol) and MeOH (10 mL).

reaction time: 3.5 h @ 55° C.

flash chromatography: SiO$_2$, from DCM/MeOH 95:5 to DCM/MeOH 75:25 yield: 67 mg (39%)

$^1$H-NMR (MeOH) δ 1.16 (d, J=6.38 Hz, 6H, 2×CH$_3$), 3.19 (t, J=6.26 Hz, 2H, CH$_2$), 3.74-3.87 (m, 3H, CH+CH$_2$), 6.52-6.54 (m, 2H, C$^3$/C$^5$—H Pyr), 7.07-7.19 (m, 2H, C$^3$/C$^5$—H-4-F-Ph), 7.43-7.51 (m, 2H, C$^2$/C$^6$—H-4-F-Ph), 7.82 (d, J=5.79 Hz, 1H, C$^6$—H-Pyr)

IR (ATR) ṽ (cm$^{-1}$) 2968, 2927, 2868, 1606, 1547, 1501, 1385, 1283, 1220 (C—F), 1158, 1014, 839, 813

2-(4-(4-Fluorophenyl)-5-(2-(tetrahydro-2H-pyran-4-ylamino)pyridin-4-yl)-1H-imidazol-2-ylthio)ethanol Example 8v

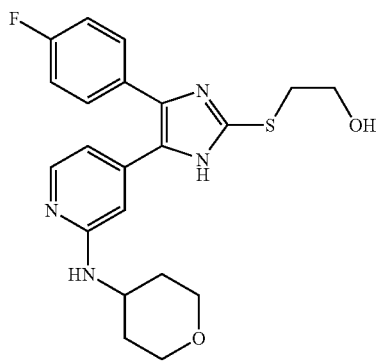

Compound 8v was prepared according to general procedure H from 7i (150 mg, 0.40 mmol), KOt-Bu (50 mg, 0.45 mmol), 2-bromoethanol (56 mg, 0.45 mol) and MeOH (10 mL).

reaction time: 3.5 h @ 55° C.

flash chromatography: SiO$_2$, from DCM/MeOH 95:5 to DCM/MeOH 75:25 yield: 82 mg (50%)

$^1$H-NMR (MeOD) δ 1.39-1.56 (m, 2H, CH$_2$), 1.86-1.92 (m, 2H, CH$_2$), 3.20 (t, J=6.21 Hz, 2H, CH$_2$), 3.48 (t, J=11.21 Hz, 2H, CH$_2$), 3.66-3.84 (m, 3H, CH+CH$_2$), 3.91-3.97 (m, 2H, CH$_2$), 6.52-6.57 (m, 2H, C$^3$/C$^5$—H Pyr), 7.11-7.20 (m, 2H, C$^3$/C$^5$—H-4-F-Ph), 7.43-7.50 (m, 2H, C$^2$—/C$^6$—H-4-F-Ph), 7.83 (d, J=4.80 Hz, 1H, C$^6$—H-Pyr)

IR (ATR) ṽ (cm$^{-1}$) 3098 (br), 2925, 2850, 1607, 1548, 1503, 1444, 1366, 1289, 1220 (C—F), 1157, 1136, 1082, 1010, 982, 839, 813

2-(4-(4-Fluorophenyl)-5-(2-(1-phenylethylamino)pyridin-4-yl)-1H-imidazol-2-ylthio)ethanol

Example 8x

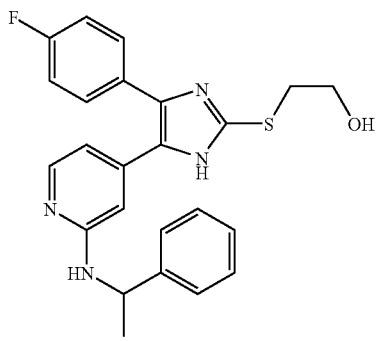

Compound 8 x was prepared according to general procedure H from 7a (300 mg, 0.77 mmol), KOt-Bu (106 mg, 0.85 mmol), 2-bromoethanol (95 mg, 0.85 mol) and MeOH (20 mL).
reaction time: 4.5 h @ 55° C.
flash chromatography: SiO$_2$, from DCM/MeOH 95:5 to DCM/MeOH 8:2
yield: 143 mg (43%)
$^1$H-NMR (MeOD) δ 1.43 (d, J=6.6 Hz, 3H, CH$_3$), 3.16 (d, J=5.9 Hz, 2H, CH$_2$), 3.63 (d, J=5.8 Hz, 2H, CH$_2$), 4.60-4.70 (m, 1H, CH), 6.49 (s, 1H, C$^3$—H-Pyr), 6.56-6.58 (m, 1H, C$^5$—H-Pyr), 7.06-7.21 (m, 7H, C$^3$/C$^5$—H-4-F-Ph+5 Ph), 7.34-7.40 (m, 2H, C$^2$/C$^6$—H-4-F-Ph), 7.79-7.91 (m, 1H, C$^6$—H-Pyr)
IR (ATR) $\tilde{v}$ (cm$^{-1}$) 2980, 1605, 1547, 1502, 1448, 1221 (C—F), 1156, 1094, 1069, 837 (Ar), 813, 760, 699 (Ar), 614, 577, 527

1-(4-Fluorphenyl)-2-(fluorpyridin-4-yl)ethanone

Example 9

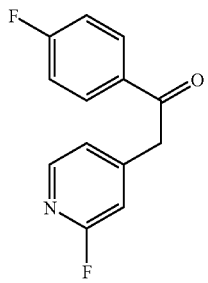

2-Fluoro-4-methylpyridine (4.44 g, 0.04 mol) and ethyl 4-fluorobenzoate (6.73 g, 0.04 mol) were dissolved in dry THF under argon atmosphere. The solution was cooled to 0° C. and NaHMDS (40 mL, 0.08 mol) was added dropwise. The mixture was allowed to stir at this temperature for 2 h and additional 1 h at room temperature. The reaction was treated with EtOAc and washed with 10% HCl (2×). The organic layer was dried over Na$_2$SO$_4$ and the solvent removed in vacuo to afford a colorless solid.
yield: 8.81 g (94%)
$^1$H-NMR (DMSO) δ4.58 (s, 2H, CH$_2$), 7.09 (s, 1H, C$^3$—H 2-F-Pyr), 7.25 (d, 1H, J=4.92 Hz, 1H, C$^5$—H 2-F-Pyr.), 7.38 (t, 2H, J=8.4 Hz, 4-F-Ph), 8.12-8.18 (m, 3H, 4-F-Ph, C$^6$—H 2-F-Pyr)
IR (ATR) $\tilde{v}$ (cm$^{-1}$) 3070, 2917, 2845, 1684 (CO), 1615, 1553, 1510, 1411, 1271, 1234 (CF), 998, 829, 813, 792

1-(4-Fluorphenyl)-2-(2-fluorpyridin-4-yl)-ethan-1,2-dion-2-oxime

Example 10

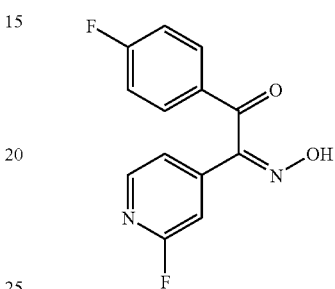

A solution of 9 (1.35 g, 5.8 mmol) in glacial acetic acid (10 mL) was cooled to 10° C. and a solution of NaNO$_2$ (1.21 g, 17.5 mmol) in water (7 mL) was added dropwise. The reaction was allowed to warm to room temperature while stirring for 0.5 h. Water was added and the mixture was stirred for another 3 h. The white precipitate was filtrated, washed with water and died in vacuo.
yield: 1.47 g (97%)
$^1$H-NMR (DMSO) δ 7.18-7.19 (m, 1H, C$^3$—H 2-F-Pyr), 7.36-7.46 (m, 3H, C$^5$—H 2-F-Pyr+C$^3$/C$^5$4-F-Ph), 7.91-7.97 (m, 2H, C$^2$/C$^6$4-F-Ph), 8.28 (dd, 1H, J=5.2 Hz, 0.6 Hz, C$^6$—H 2-F-Pyr), 12.72 (bs, 1H, NOH)
IR (ATR) $\tilde{v}$ (cm$^{-1}$) 2841, 1667 (CO), 1594, 1262, 1234 (CF), 1154, 995, 945, 869, 838, 663

2-Amino-1-(4-fluorphenyl)-2-(2-fluorpyridin-4-yl)ethanone hydrochloride

Example 11

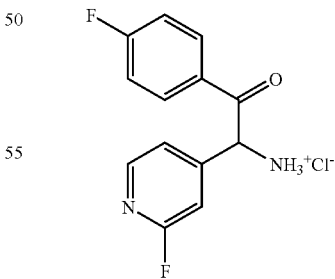

Compound 10 (2.01 g, 0.077 mol) was dissolved in isopropanol (25 mL) and saturated isopropanolic hydrogen chloride (25 mL). Pd/C 10% (0.35 g) was added. The reaction flask was evacuated and flushed with hydrogen gas (4×). The suspension was agitated at room temperature under hydrogen atmosphere at atmospheric pressure for 6 h. The catalyst was filtered off and washed thoroughly with methanol. The filtrate was concentrated in vacuo to afford a yellowish solid.

yield: 2.20 g (100%)

$^1$H-NMR (DMSO) δ 6.56 (s, 1H, CH), 7.32-7.41 (m, 2H, 4-F-Ph), 7.51-7.53 (m, 2H, $C^3/C^5$—H 2-F-Pyr), 8.17-8.28 (m, 2H, 4-F-Ph), 8.30 (d, J=5.8 Hz, 1H, $C^6$—H 2-F-Pyr), 9.36 (bs, 3H, $NH_3^+$)

IR (ATR) ṽ (cm$^{-1}$) 2809 ($NH_3^+$), 2619, 1695 (CO), 1618, 1597, 1520, 1509, 1418, 1281, 1255, 1239 (CF), 1164, 970, 848, 833, 792

4-(4-Fluorphenyl)-5-(2-fluorpyridin-4-yl)-1,3-dihydroimidazol-2-thione

Example 12

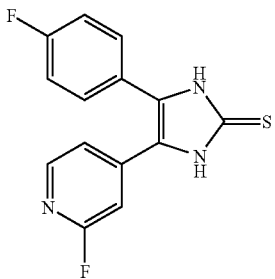

Compound 11 (0.43 g, 1.5 mmol) was dissolved in absolute MeOH and potassium thiocyanate (0.03 g, 3.1 mmol) was added. The reaction mixture was heated to reflux for 1.5 h forming a yellow precipitate. The suspension was cooled to room temperature and slowly diluted with water (40 mL). The yellow precipitate was filtered off, washed with water and dried.

yield: 0.27 g (62%)

$^1$H-NMR (DMSO) δ 7.10-7.13 (m, 2H, $C^3$—/$C^5$—H 2-F-Pyr), 7.27-7.35 (m, 2H, 4-F-Ph), 7.45-7.52 (m, 2H, 4-F-Ph), 8.12 (d, J=5.1 Hz, 1H, $C^6$—H 2-F-Pyr), 12.82 (bs, 2H, NH)

IR (ATR) ṽ (cm$^{-1}$) 2889, 1614, 1517, 1498 (C(S)NH), 1416, 1223 (CF), 1157, 1003, 843, 830, 815

2-(4-(4-Fluorphenyl)-5-(2-fluorpyridin-4-yl)-1H-imidazol-2-ylthio)ethanol

Example 13

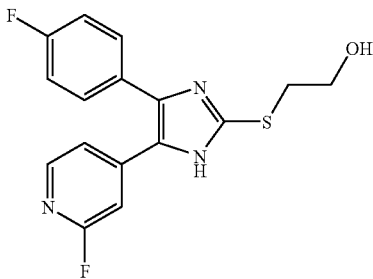

Compound 12 (0.87 g, 3 mmol) and 2-bromoethanol (0.41 g 3.3 mmol) were suspended in absolute MeOH (35 mL) and sodium ethoxide (0.25 g, 3.6 mmol) was added. The reaction mixture was stirred for 4 h at rt, the solvent was removed and the crude product was purified by flash chromatography (SiO$_2$, DCM/MeOH 9-1) to afford a colorless solid.

yield: 0.58 g (58%)

$^1$H-NMR (DMSO) δ 3.20-3.26 (m, 2H, $CH_2$), 3.65-3.72 (m, 2H, $CH_2$), 7.08 (s, 1H, $C^3$—H-Pyr), 7.26-7.35 (m, 3H, $C^5$—H-Pyr, $C^3$—/$C^5$-4-F-Ph), 7.48-7.55 (m, 2H, $C^2$—/$C^6$-4-F-Ph), 8.09 (d, J=5.1 Hz, 1H, $C^6$—H 2-F-Pyr)

IR (ATR) ṽ (cm$^{-1}$) 312, 2853, 1610, 1540, 1497, 1420, 1401, 1290, 1227 (CF), 1203, 1159, 1080, 1021, 1000, 989, 882, 837, 816

(1R,4R)-4-(4-(4-(4-Fluorophenyl)-2-(2-hydroxyethylthio)-1H-imidazol-5-yl)pyridin-2-ylamino)cyclohexanol

Example 8w

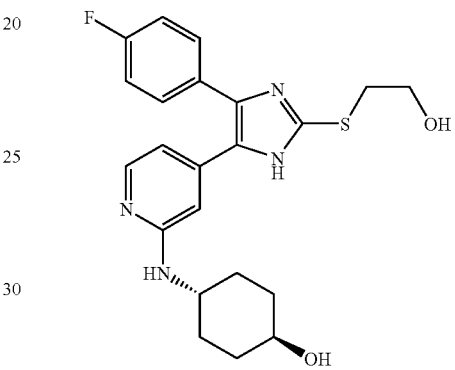

Compound 8w was prepared by irradiating 12 (160 mg, 0.48 mmol) and trans-4-aminocylohexanol (440 mg, 3.84 mmol) in a sealed tube at 135° C. for 3.5 h, by moderating the initial microwave power (250 W). After cooling down to room temperature in a stream of compressed air the yellow solid was dissolved in MeOH, transferred in a round-bottomed flask and the solvent was evaporated. The crude product was purified by flash chromatography (SiO$_2$, from DCM/MeOH 95:5 to DCM/MeOH 75:25).

yield: 82 mg (40%)

$^1$H-NMR (MeOD) δ 1.18-1.38 (m, 4H, 2×$CH_2$), 1.93-2.07 (m, 4H, 2×$CH_2$), 1.65-1.81 (m, 1H, CH), 3.19 (t, J=6.24 Hz, $CH_2$), 3.39-3.55 (m, 2H, 2×CH), 3.81 (t, J=6.23 Hz, $CH_2$), 6.50-6.56 (m, 2H, $C^3/C^5$—H-Pyr), 7.10-7.19 (m, 2H, $C^3/C^6$—H-4-F-Ph), 7.43-7.50 (m, 2H, $C^2/C^6$—H-4-F-Ph), 7.82 (d, J=5.24 Hz, 1H, $C^6$—H-Pyr)

IR (ATR) ṽ (cm$^{-1}$) 3106 (br), 2930, 2857, 1607, 1548, 1502, 1451, 1366, 1221 (C—F), 1157, 1053, 988 957, 839, 814

P38α Enzyme Inhibition Assay:

First the microtiter plates are coated using a dilution of ATF-2, substrate of p38α. Each step is followed by a threefold washing step. As the substrate doesn't cover the whole surface, blocking buffer is used to capture the free binding sites. In the meantime, the test compounds are diluted using the kinase buffer, which contains ATP [100 μM], phosphatase-inhibitors and the activated p38α.

The different dilutions of the test compounds are pipetted on the plate. ATP and the compounds compete for the enzyme's binding site. During an incubation time of 60 minutes ATF-2 is dual phosphorylated at Thr 69/71 by p38α kinase depending on its degree of inhibition. Next the first antibody is added into the wells. This antibody binds specifically at dual phosphorylated ATF-2 (Thr 69/71). Secondary antibody, that is conjugated with alkaline phosphatase, binds at the first one. Finally 4-NPP is given in the wells and after an incubation under cover of darkness it is photometrically analysed (405 nm).

P38 Enzyme Inhibition Results

Results of the enzyme inhibition assay are shown in the Table.

| Ex. No. | Compound | Kinase assay IC$_{50}$ (mol/l) |
|---|---|---|
|  | [4-(4-fluorophenyl)-5-(pyridin-4-yl)-1H-imidazol-2-ylthio-propane-1,2-diol] | $3.6*10^{-6}$ |
| 8a | [4-(4-fluorophenyl)-5-(2-(1-phenylethylamino)pyridin-4-yl)-1H-imidazol-2-ylthio-propane-1,2-diol] | $4.2*10^{-8}$ |
| 8b | [4-(4-fluorophenyl)-5-(2-benzylaminopyridin-4-yl)-1H-imidazol-2-ylthio-propane-1,2-diol] | $8.7*10^{-8}$ |
| 8c | [4-(4-fluorophenyl)-5-(2-isobutylaminopyridin-4-yl)-1H-imidazol-2-ylthio-propane-1,2-diol] | $1.3*10^{-8}$ |
| 8d | [4-(4-fluorophenyl)-5-(2-ethylaminopyridin-4-yl)-1H-imidazol-2-ylthio-propane-1,2-diol] | $2.6*10^{-8}$ |
| 8e | [4-(4-fluorophenyl)-5-(2-methylaminopyridin-4-yl)-1H-imidazol-2-ylthio-propane-1,2-diol] | $1.0*10^{-7}$ |
| 8f | [4-(4-fluorophenyl)-5-(2-(2-methylbutylamino)pyridin-4-yl)-1H-imidazol-2-ylthio-propane-1,2-diol] | $1.4*10^{-8}$ |
| 8g | [4-(4-fluorophenyl)-5-(2-(sec-butylamino)pyridin-4-yl)-1H-imidazol-2-ylthio-propane-1,2-diol] | $5.1*10^{-9}$ |

| Ex. No. | Compound | Kinase assay IC$_{50}$ (mol/l) |
|---|---|---|
| 8h | 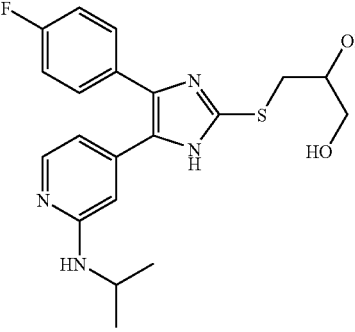 | $3.6 \times 10^{-9}$ |
| 8i | 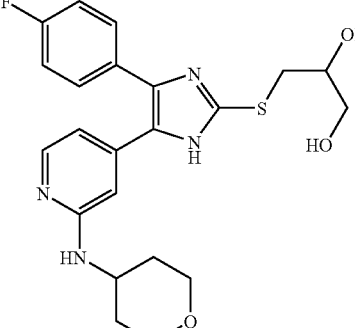 | $3.3 \times 10^{-9}$ |
| 8j | 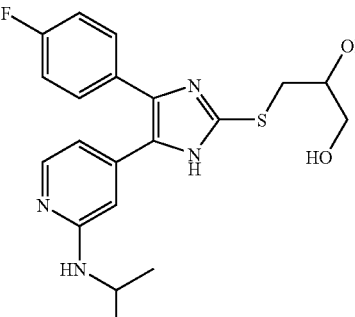 | $1.2 \times 10^{-8}$ |
| 8k | 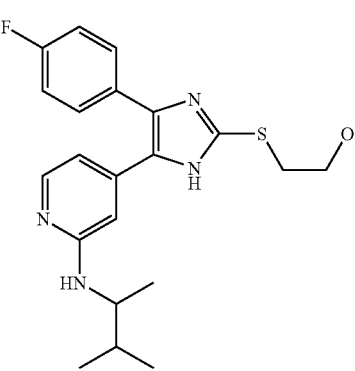 | $1.0 \times 10^{-8}$ |
| 8l | 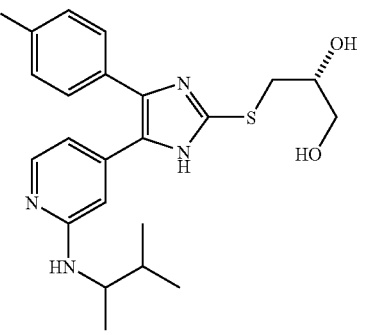 | $1.7 \times 10^{-8}$ |
| 8m | 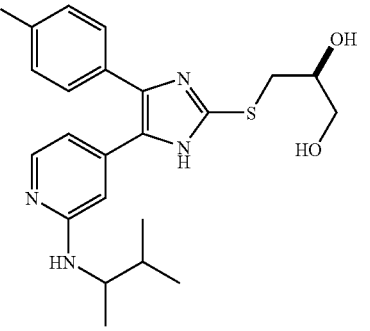 | $9.5 \times 10^{-9}$ |
| 8n | 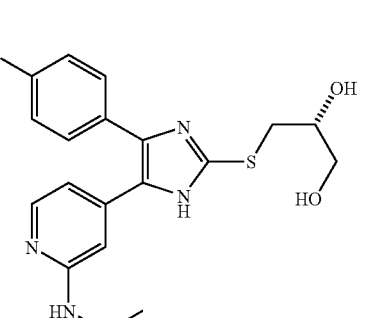 | $5.5 \times 10^{-9}$ |
| 8o | 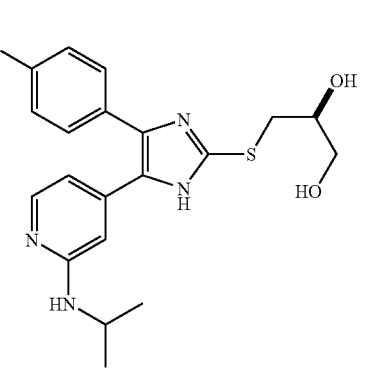 | $3.2 \times 10^{-9}$ |

| Ex. No. | Compound | Kinase assay IC$_{50}$ (mol/l) | Ex. No. | Compound | Kinase assay IC$_{50}$ (mol/l) |
|---|---|---|---|---|---|
| 8p | | 3.5*10$^{-8}$ | 8t | | 3.6*10$^{-9}$ |
| 8q | | 3.6*10$^{-8}$ | 8u | | 3.0*10$^{-9}$ |
| 8r | | 4.0*10$^{-7}$ | 8v | | 2.3*10$^{-9}$. |
| 8s | | 2.0*10$^{-8}$ | 8w | | 2.0*10$^{-9}$. |
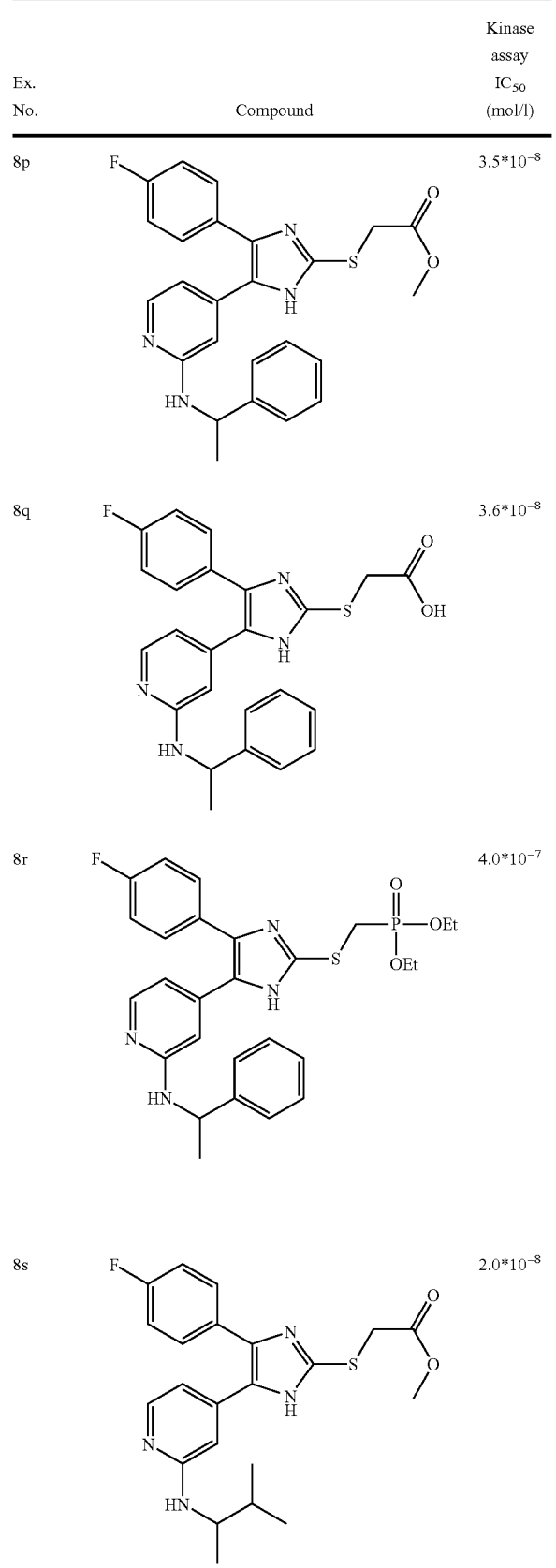
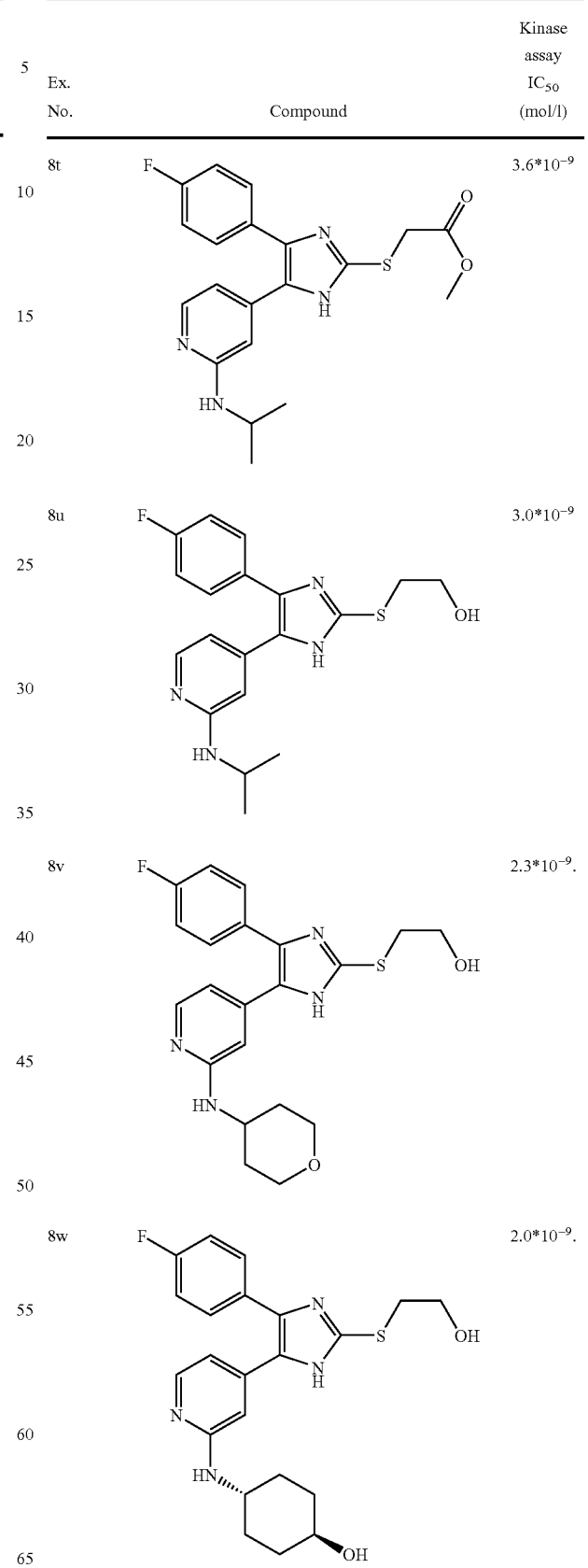

| Ex. No. | Compound | Kinase assay IC$_{50}$ (mol/l) |
|---|---|---|
| 8x | 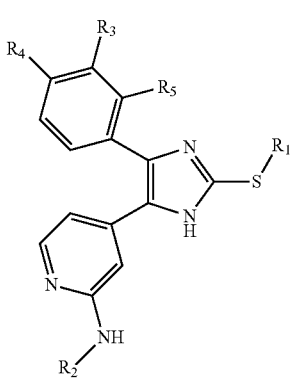 | $1.4 \times 10^{-8}$ |

The invention claimed is:
1. A compound represented by the structure:

$$\text{[structure with R}_3\text{, R}_4\text{, R}_5 \text{ on phenyl; imidazole with SR}_1\text{; pyridine with NHR}_2\text{]}$$

wherein:
$R_1$ = 2-hydroxypropyl;
3-hydroxypropyl;
2-hydroxyethyl;
2,3-dihydroxypropyl;
2-hydroxy-3-aminopropyl;
2-hydroxy-3-aminobutyl;
3,4-dihydroxybutyl;
2,3,4-trihydroxybutyl;
—(CH$_2$)$_n$—COR, in which R=OH, O-alkyl (C$_1$-C$_4$), O-alkylaryl, NH$_2$, NHMe, or NHOH, and n=1, 2, 3, 4, 5;
—CH$_2$—P=O(OR)$_2$ in which R=H, CH$_3$, or CH$_2$CH$_3$;
—CH$_2$—(CH$_2$)$_m$—S(=O)$_n$—R, in which R=alkyl (C$_1$-C$_5$), OH, NH$_2$, and m=1, 2, 3 and n=0, 1, 2;
Glycidyl;
3-methylglycidyl;
—CH$_2$—CHOH—COR, in which R=OH, OMe, OEt, NH$_2$, or NHOH;
—CH(CH$_2$OH)—COR, in which R=OH, OMe, OEt, NH$_2$, or NHOH;
—CH$_2$—CHOH—CN; or
—CH(CH$_2$OH)—CN;
$R_2$ = methyl;
ethyl;
isopropyl;
sec-butyl;
isobutyl;
2-(3-methyl)butyl;
cyclopropyl;
cyclobutyl;
cyclopentyl;
cyclohexyl;
morpholinyl;
tetrahydropyranyl;
phenylethyl;
benzyl;
methylcyclohexyl;
methylcyclopentyl;
methylmorpholinyl;
hydroxycyclohexyl; or
hydroxycyclopentyl;
$R_3$ = H, halogen, CF$_3$, or OCF$_3$;
$R_4$ = H, halogen, CF$_3$, or OCF$_3$; and
$R_5$ = H, halogen, or CF$_3$;
or a salt thereof.

2. A pharmaceutical composition comprising a compound or salt of claim 1 and a pharmaceutically acceptable excipient, carrier or diluent.

3. A method of treating a disease in a patient in need of such treatment, comprising administering an effective amount of a compound according to claim 1, to a patient in need thereof; wherein the disease is selected from Alzheimer's disease, stroke, diabetes, obesity, and inflammation.

4. The method of claim 3, wherein the patient is in need of treatment for inflammation.

5. A method of treating an inflammatory disorder, comprising administering a therapeutically effective amount of a compound according to claim 1 to a patient in need thereof.

6. The method of claim 5, wherein the inflammatory disorder is a chronic inflammation.

7. The method of claim 5, wherein the inflammatory disorder is an inflammatory bowel disease.

8. The method of claim 7, wherein the inflammatory bowel disease is Crohn's disease, ulcerative colitis, collagenous colitis, lymphocytic colitis, ischaemic colitis, diversion colitis, Behcet's syndrome, infective colitis or indeterminate colitis.

9. The method of claim 5, wherein the inflammatory disorder is psoriasis.

10. The method of claim 9, wherein the psoriasis is plaque psoriasis, pustular psoriasis, guttate psoriasis, psoriatic arthritis, inverse psoriasis or erythrodermic psoriasis.

11. The method of claim 5, wherein the inflammatory disorder is sarcoidosis, rheumatoid arthritis, asthma, chronic obstructive pulmonary disease, or atherosclerosis.

* * * * *